(12) United States Patent  
Kim et al.

(10) Patent No.: US 9,561,096 B2
(45) Date of Patent: Feb. 7, 2017

(54) DEVICES AND METHODS FOR TREATMENT OF VASCULAR ANEURYSMS

(71) Applicant: Thomas J. Fogarty, Portola Valley, CA (US)

(72) Inventors: Steven W. Kim, Los Altos, CA (US); Brian K. Shiu, Sunnyvale, CA (US)

(73) Assignee: Thomas J. Fogarty, Mountain View, CA (US)

( * ) Notice: Subject to any disclaimer, the term of this patent is extended or adjusted under 35 U.S.C. 154(b) by 168 days.

(21) Appl. No.: 14/225,730

(22) Filed: Mar. 26, 2014

(65) Prior Publication Data

US 2014/0207226 A1 Jul. 24, 2014

Related U.S. Application Data

(63) Continuation of application No. 14/087,980, filed on Nov. 22, 2013, now Pat. No. 8,936,633, which is a
(Continued)

(51) Int. Cl.
*A61F 2/06* (2013.01)
*A61F 2/07* (2013.01)
(Continued)

(52) U.S. Cl.
CPC .............. *A61F 2/07* (2013.01); *A61B 17/1219* (2013.01); *A61B 17/12022* (2013.01);
(Continued)

(58) Field of Classification Search
CPC ................... A61B 17/12113; A61B 17/12118; A61B 2018/00416; A61F 2/07; A61F 2/95; A61F 2002/077; A61F 2002/823
See application file for complete search history.

(56) References Cited

U.S. PATENT DOCUMENTS 2,903,365 A 9/1959 O'Brian et al.
4,085,757 A 4/1978 Pevsner
(Continued)

FOREIGN PATENT DOCUMENTS

AU 2003/204493 4/2004
FR 2689388 10/1993
(Continued)

OTHER PUBLICATIONS

Franklin et al, "Uptake of Tetracycline by Aortic Aneurysm Wall and its Effect on Inflammation and Proteolysis," *Brit. J. Surgery*, 86(6):771-775, 1999.
(Continued)

*Primary Examiner* — Ryan J Severson
(74) *Attorney, Agent, or Firm* — Levine Bagade Han LLP

(57) ABSTRACT

The present invention relates to devices and methods for the treatment of diseases in the vasculature, and more specifically, devices and methods for treatment of aneurysms found in blood vessels. In a first embodiment of the present invention, a two part prostheses, where one part is an expandable sponge structure and the other part is an expandable tubular mesh structure, is provided. In the first embodiment, the expandable sponge structure is intended to fill the aneurysm cavity to prevent further dilatation of the vessel wall by creating a buffer or barrier between the pressurized pulsating blood flow and the thinning vessel wall. In the first embodiment, the expandable tubular mesh structure is placed across the aneurysm, contacting the inner wall of healthy vessel proximal and distal to the aneurysm.

20 Claims, 26 Drawing Sheets

Related U.S. Application Data continuation of application No. 13/663,272, filed on Oct. 29, 2012, now Pat. No. 8,647,377, which is a continuation of application No. 13/533,658, filed on Jun. 26, 2012, now Pat. No. 8,535,367, which is a continuation of application No. 11/552,913, filed on Oct. 25, 2006, now Pat. No. 8,231,665, which is a continuation of application No. 10/301,061, filed on Nov. 20, 2002, now abandoned.

(60) Provisional application No. 60/333,373, filed on Nov. 26, 2001.

(51) Int. Cl.
| | | |
|---|---|---|
| *A61B 17/12* | (2006.01) | |
| *A61F 2/958* | (2013.01) | |
| *A61F 2/90* | (2013.01) | |
| *A61F 2/954* | (2013.01) | |
| *A61B 17/00* | (2006.01) | |
| *A61B 17/34* | (2006.01) | |
| *A61F 2/82* | (2013.01) | |

(52) U.S. Cl.
CPC .. *A61B 17/12036* (2013.01); *A61B 17/12118* (2013.01); *A61B 17/12136* (2013.01); *A61B 17/12186* (2013.01); *A61B 17/12195* (2013.01); *A61F 2/90* (2013.01); *A61F 2/954* (2013.01); *A61F 2/958* (2013.01); *A61B 2017/00898* (2013.01); *A61B 2017/00986* (2013.01); *A61B 2017/1205* (2013.01); *A61B 2017/3484* (2013.01); *A61F 2002/065* (2013.01); *A61F 2002/077* (2013.01); *A61F 2002/823* (2013.01)

(56) References Cited

U.S. PATENT DOCUMENTS

| | | | |
|---|---|---|---|
| 4,108,173 | A | 8/1978 | Silvenko |
| 4,301,803 | A | 11/1981 | Handa et al. |
| 4,346,712 | A | 8/1982 | Handa et al. |
| 4,553,545 | A | 11/1985 | Maass et al. |
| 4,577,631 | A | 3/1986 | Kreamer |
| 4,638,803 | A | 1/1987 | Rand |
| 4,641,653 | A | 2/1987 | Rockey |
| 4,728,328 | A | 3/1988 | Hughes et al. |
| 4,944,745 | A | 7/1990 | Sogard et al. |
| 4,994,069 | A | 2/1991 | Ritchart et al. |
| 5,078,726 | A | 1/1992 | Kreamer |
| 5,104,404 | A | 4/1992 | Wolff |
| 5,133,731 | A | 7/1992 | Butler et al. |
| 5,151,105 | A | 9/1992 | Kwan-Gett |
| 5,156,620 | A | 10/1992 | Pigott |
| 5,163,953 | A | 11/1992 | Vince |
| 5,192,301 | A | 3/1993 | Kamiya et al. |
| 5,226,911 | A | 7/1993 | Chee et al. |
| 5,282,824 | A | 2/1994 | Gianturco |
| 5,308,356 | A | 5/1994 | Blackshear, Jr. et al. |
| 5,312,415 | A | 5/1994 | Palermo |
| 5,330,528 | A | 7/1994 | Lazim |
| 5,334,217 | A | 8/1994 | Das |
| 5,360,443 | A | 11/1994 | Barone et al. |
| 5,395,333 | A | 3/1995 | Brill |
| 5,411,550 | A | 5/1995 | Herweck et al. |
| 5,478,309 | A | 12/1995 | Sweezer et al. |
| 5,530,528 | A | 6/1996 | Houki et al. |
| 5,534,024 | A | 7/1996 | Rogers et al. |
| 5,540,711 | A | 7/1996 | Kieturakis et al. |
| 5,558,642 | A | 9/1996 | Schweich, Jr. et al. |
| 5,575,817 | A | 11/1996 | Martin |
| 5,578,071 | A | 11/1996 | Parodi |
| 5,582,619 | A | 12/1996 | Ken |
| 5,591,195 | A | 1/1997 | Taheri et al. |
| 5,593,442 | A | 1/1997 | Klein |
| 5,613,981 | A | 3/1997 | Boyle et al. |
| 5,628,783 | A | 5/1997 | Quiachon et al. |
| 5,665,117 | A | 9/1997 | Rhodes |
| 5,667,767 | A | 9/1997 | Greff et al. |
| 5,693,088 | A | 12/1997 | Lazarus |
| 5,702,361 | A | 12/1997 | Evans et al. |
| 5,713,917 | A | 2/1998 | Leonhardt et al. |
| 5,725,568 | A | 3/1998 | Hastings |
| 5,728,131 | A | 3/1998 | Frantzen et al. |
| 5,749,894 | A | 5/1998 | Engelson |
| 5,752,974 | A | 5/1998 | Rhee et al. |
| 5,766,160 | A | 6/1998 | Samson et al. |
| 5,769,882 | A | 6/1998 | Fogarty et al. |
| 5,785,679 | A | 7/1998 | Abolfathi et al. |
| 5,795,331 | A | 8/1998 | Cragg et al. |
| 5,800,526 | A | 9/1998 | Anderson et al. |
| 5,823,198 | A | 10/1998 | Jones et al. |
| 5,824,037 | A | 10/1998 | Fogarty et al. |
| 5,824,040 | A | 10/1998 | Cox et al. |
| 5,830,230 | A | 11/1998 | Berryman et al. |
| 5,843,160 | A | 12/1998 | Rhodes |
| 5,861,003 | A | 1/1999 | Latson et al. |
| 5,876,448 | A | 3/1999 | Thompson et al. |
| 5,916,235 | A | 6/1999 | Guglielmi |
| 5,925,059 | A | 7/1999 | Palermo et al. |
| 5,928,260 | A | 7/1999 | Chin et al. |
| 5,935,145 | A | 8/1999 | Villar et al. |
| 5,944,733 | A | 8/1999 | Engelson |
| 5,951,599 | A | 9/1999 | McCrory |
| 5,980,514 | A | 11/1999 | Kupiecki et al. |
| 5,984,963 | A | 11/1999 | Ryan et al. |
| 5,994,750 | A | 11/1999 | Yagi |
| 6,015,424 | A | 1/2000 | Rosenbluth et al. |
| 6,015,431 | A | 1/2000 | Thornton et al. |
| 6,024,754 | A | 2/2000 | Engelson |
| 6,059,823 | A | 5/2000 | Holman et al. |
| 6,063,121 | A | 5/2000 | Xavier et al. |
| 6,066,149 | A | 5/2000 | Samson et al. |
| 6,080,194 | A | 6/2000 | Pachence et al. |
| 6,093,199 | A | 7/2000 | Brown et al. |
| 6,096,021 | A | 8/2000 | Helm et al. |
| 6,102,940 | A | 8/2000 | Robichon et al. |
| 6,110,198 | A | 8/2000 | Fogarty et al. |
| 6,113,629 | A | 9/2000 | Ken |
| 6,136,015 | A | 10/2000 | Kurz et al. |
| 6,139,520 | A | 10/2000 | McCrory et al. |
| 6,146,373 | A | 11/2000 | Cragg et al. |
| 6,149,664 | A | 11/2000 | Kurz |
| 6,152,956 | A | 11/2000 | Pierce |
| 6,165,193 | A | 12/2000 | Greene, Jr. et al. |
| 6,165,194 | A | 12/2000 | Denardo |
| 6,168,592 | B1 | 1/2001 | Kupiecki et al. |
| 6,190,402 | B1 | 2/2001 | Horton et al. |
| 6,193,745 | B1 | 2/2001 | Fogarty et al. |
| 6,196,230 | B1 | 3/2001 | Hall et al. |
| 6,203,550 | B1 | 3/2001 | Olson |
| 6,203,779 | B1 | 3/2001 | Ricci et al. |
| 6,214,036 | B1 | 4/2001 | Letendre et al. |
| 6,231,562 | B1 | 5/2001 | Khosravi et al. |
| 6,238,403 | B1 | 5/2001 | Greene, Jr. et al. |
| 6,248,122 | B1 | 6/2001 | Klumb et al. |
| 6,257,335 | B1 | 7/2001 | Nguyen et al. |
| 6,261,305 | B1 | 7/2001 | Marotta et al. |
| 6,273,909 | B1 | 8/2001 | Kugler et al. |
| 6,273,917 | B1 | 8/2001 | Inoue |
| 6,283,991 | B1 | 9/2001 | Cox et al. |
| 6,287,315 | B1 | 9/2001 | Wijeratne et al. |
| 6,290,731 | B1 | 9/2001 | Solovay et al. |
| 6,293,960 | B1 | 9/2001 | Ken |
| 6,296,603 | B1 | 10/2001 | Turnlund et al. |
| 6,296,604 | B1 | 10/2001 | Garibaldi et al. |
| 6,299,597 | B1 | 10/2001 | Buscemi et al. |
| 6,299,619 | B1 | 10/2001 | Greene, Jr. et al. |
| 6,312,421 | B1 | 11/2001 | Boock |
| 6,312,462 | B1 | 11/2001 | McDermott et al. |
| 6,312,463 | B1 | 11/2001 | Rourke et al. |
| 6,315,709 | B1 | 11/2001 | Garibaldi et al. |
| 6,319,276 | B1 | 11/2001 | Holman et al. |

(56) References Cited

U.S. PATENT DOCUMENTS

| | | |
|---|---|---|
| 6,325,819 B1 | 12/2001 | Pavcnik et al. |
| 6,331,184 B1 | 12/2001 | Abrams |
| 6,334,869 B1 | 1/2002 | Leonhardt et al. |
| 6,344,041 B1 | 2/2002 | Kupiecki et al. |
| 6,344,048 B1 | 2/2002 | Chin et al. |
| 6,344,056 B1 | 2/2002 | Dehdashtian |
| 6,350,270 B1 | 2/2002 | Roue |
| 6,358,556 B1 | 3/2002 | Ding et al. |
| 6,361,556 B1 | 3/2002 | Chuter |
| 6,364,823 B1 | 4/2002 | Garibaldi et al. |
| 6,375,668 B1 | 4/2002 | Gifford et al. |
| 6,375,669 B1 | 4/2002 | Rosenbluth et al. |
| 6,379,329 B1 | 4/2002 | Naglreiter et al. |
| 6,383,174 B1 | 5/2002 | Eder |
| 6,395,019 B2 | 5/2002 | Chobotov |
| 6,409,757 B1 | 6/2002 | Trout, III et al. |
| 6,458,119 B1 | 10/2002 | Berenstein et al. |
| 6,463,317 B1 | 10/2002 | Kucharczyk et al. |
| 6,485,510 B1 | 11/2002 | Camrud et al. |
| 6,494,889 B1 | 12/2002 | Fleischman et al. |
| 6,506,204 B2 | 1/2003 | Mazzocchi |
| 6,511,468 B1 | 1/2003 | Cragg et al. |
| 6,521,244 B1 | 2/2003 | Kanesaka |
| 6,527,739 B1 | 3/2003 | Bigus et al. |
| 6,544,276 B1 | 4/2003 | Azizi |
| 6,551,280 B1 | 4/2003 | Knighton et al. |
| 6,551,303 B1 | 4/2003 | Van Tassel et al. |
| 6,558,367 B1 | 5/2003 | Cragg et al. |
| 6,565,602 B2 | 5/2003 | Rolando et al. |
| 6,585,756 B1 | 7/2003 | Strecker |
| 6,585,760 B1 | 7/2003 | Fogarty |
| 6,589,265 B1 | 7/2003 | Palmer et al. |
| 6,592,614 B2 | 7/2003 | Lenker et al. |
| 6,613,037 B2 | 9/2003 | Khosravi et al. |
| 6,613,074 B1 | 9/2003 | Mitelberg et al. |
| 6,616,684 B1 | 9/2003 | Vidlund et al. |
| 6,626,928 B1 | 9/2003 | Raymond et al. |
| 6,626,938 B1 | 9/2003 | Butaric et al. |
| 6,629,947 B1 | 10/2003 | Sahatjian et al. |
| 6,645,167 B1 | 11/2003 | Whalen, II et al. |
| 6,656,214 B1 | 12/2003 | Fogarty et al. |
| 6,663,607 B2 | 12/2003 | Slaikeu et al. |
| 6,663,667 B2 | 12/2003 | Dehdashtian et al. |
| 6,692,510 B2 | 2/2004 | West |
| 6,695,876 B2 | 2/2004 | Marotta et al. |
| 6,712,826 B2 | 3/2004 | Lui |
| 6,723,108 B1 | 4/2004 | Jones et al. |
| 6,729,356 B1 | 5/2004 | Baker et al. |
| 6,730,119 B1 | 5/2004 | Smalling |
| 6,764,510 B2 | 7/2004 | Vidlund et al. |
| 6,827,735 B2 | 12/2004 | Greenberg |
| 6,843,803 B2 | 1/2005 | Ryan et al. |
| 6,852,097 B1 | 2/2005 | Fulton, III |
| 6,921,410 B2 | 7/2005 | Porter |
| 7,070,609 B2 | 7/2006 | West |
| 7,070,616 B2 | 7/2006 | Majercak et al. |
| 7,081,129 B2 | 7/2006 | Chobotov |
| 7,101,396 B2 | 9/2006 | Artof et al. |
| 7,128,736 B1 | 10/2006 | Abrams et al. |
| 7,147,660 B2 | 12/2006 | Chobotov et al. |
| 7,147,661 B2 | 12/2006 | Chobotov et al. |
| 7,530,988 B2 | 5/2009 | Evans et al. |
| 7,615,071 B2 | 11/2009 | Chobotov |
| 7,708,771 B2 | 5/2010 | Chuter et al. |
| 8,231,665 B2 | 7/2012 | Kim et al. |
| 8,231,666 B2 | 7/2012 | Kim et al. |
| 8,262,686 B2 | 9/2012 | Fogarty et al. |
| 8,361,136 B2 | 1/2013 | Chobotov |
| 8,535,367 B2 | 9/2013 | Kim et al. |
| 8,562,662 B2 | 10/2013 | Kim et al. |
| 8,647,377 B2 | 2/2014 | Kim et al. |
| 8,801,769 B2 | 8/2014 | Chobotov |
| 8,936,633 B2 | 1/2015 | Kim et al. |
| 9,295,569 B2 | 3/2016 | Kim et al. |
| 2001/0020184 A1 | 9/2001 | Dehdashtian et al. |
| 2001/0044621 A1 | 11/2001 | Klumb et al. |
| 2001/0047202 A1 | 11/2001 | Slaikeu et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0052643 A1 | 5/2002 | Wholey et al. |
| 2002/0058986 A1 | 5/2002 | Landau et al. |
| 2002/0065542 A1 | 5/2002 | Lax et al. |
| 2002/0077693 A1 | 6/2002 | Barclay et al. |
| 2002/0082638 A1 | 6/2002 | Porter et al. |
| 2002/0082682 A1 | 6/2002 | Barclay et al. |
| 2002/0099441 A1 | 7/2002 | Dehdashtian |
| 2002/0107565 A1 | 8/2002 | Greenhalgh |
| 2002/0151957 A1 | 10/2002 | Kerr |
| 2002/0169497 A1 | 11/2002 | Wholey et al. |
| 2002/0183841 A1 | 12/2002 | Cohn et al. |
| 2002/0193821 A1 | 12/2002 | Trout |
| 2003/0004531 A1 | 1/2003 | Jones et al. |
| 2003/0014075 A1 | 1/2003 | Rosenbluth et al. |
| 2003/0028209 A1 | 2/2003 | Teoh et al. |
| 2003/0051735 A1 | 3/2003 | Pavcnik et al. |
| 2003/0074017 A1 | 4/2003 | Shah |
| 2003/0130724 A1 | 7/2003 | DePalma et al. |
| 2003/0171805 A1 | 9/2003 | Berg et al. |
| 2003/0195607 A1 | 10/2003 | Trout et al. |
| 2003/0204246 A1 | 10/2003 | Chu et al. |
| 2003/0216802 A1 | 11/2003 | Chobotov |
| 2003/0220666 A1 | 11/2003 | Mirigian et al. |
| 2003/0220667 A1 | 11/2003 | van der Burg et al. |
| 2003/0229286 A1 | 12/2003 | Lenker |
| 2004/0044358 A1 | 3/2004 | Khosravi et al. |
| 2004/0044361 A1 | 3/2004 | Frazier et al. |
| 2004/0073190 A1 | 4/2004 | Deem et al. |
| 2004/0073288 A1 | 4/2004 | Kerr |
| 2004/0098027 A1 | 5/2004 | Teoh et al. |
| 2004/0116997 A1 | 6/2004 | Taylor et al. |
| 2004/0186556 A1 | 9/2004 | Hogendijk et al. |
| 2004/0210249 A1 | 10/2004 | Fogarty et al. |
| 2004/0254625 A1 | 12/2004 | Stephens et al. |
| 2006/0292206 A1 | 12/2006 | Kim et al. |
| 2007/0050008 A1 | 3/2007 | Kim et al. |
| 2007/0055355 A1 | 3/2007 | Kim et al. |
| 2007/0061005 A1 | 3/2007 | Kim et al. |
| 2008/0275536 A1* | 11/2008 | Zarins .................. A61F 2/07 623/1.11 |
| 2012/0179192 A1 | 7/2012 | Fogarty et al. |
| 2012/0265287 A1 | 10/2012 | Sharma et al. |
| 2012/0330343 A1 | 12/2012 | Kim et al. |
| 2013/0060320 A1 | 3/2013 | Fogarty et al. |
| 2014/0081374 A1 | 3/2014 | Kim et al. |
| 2014/0088690 A1 | 3/2014 | Fogarty et al. |
| 2014/0142685 A1 | 5/2014 | Kim et al. |

FOREIGN PATENT DOCUMENTS

| | | |
|---|---|---|
| WO | WO 99/16384 | 4/1999 |
| WO | WO 99/43273 | 9/1999 |
| WO | WO 99/65418 | 12/1999 |
| WO | WO 00/69367 | 11/2000 |
| WO | WO 01/06950 | 2/2001 |
| WO | WO 01/28434 | 4/2001 |
| WO | WO 01/93920 | 12/2001 |
| WO | WO 02/102282 | 12/2002 |
| WO | WO 2004/045393 | 6/2004 |

OTHER PUBLICATIONS

Pyo et al, "Targeted Gene Disruption of Matrix Metalloproteinase-9 (Gelatinase B) Suppresses Development of Experimental Abdominal Aortic Aneurysms," *J. Clinical Investigation*, 105(11):1641-1649, 2000.

Tambiah et al, "Provocation of Experimental Aortic Inflammation Mediators and Chlamydia Pneumoniae," *Brit. J. Surgery*, 88(7):935-940, 2001.

Villareal et al, "Early Results Using Bare Metal Stents With or Without Coil Embolization for AAA Exclusion," *Journal of endovascular therapy : an official journal of the International*

(56) References Cited

OTHER PUBLICATIONS

*Society of Endovascular Specialists*, 8 pages, 2001.
Walton, et al, "Inhibition of Prostoglandin E2 Synthesis in Abdominal Aortic Aneurysms," *Circulation*, pp. 48-54, Jul. 6, 1999.
Xu et al, "Sp 1 Increases Expression of Cyclooxygenase-2 in Hypoxic Vascular Endothelium," *J. Biological Chemistry*, 275(32):24583-24589, 2000.

\* cited by examiner

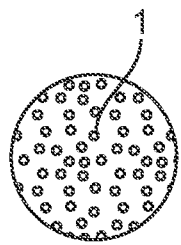 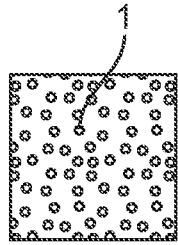 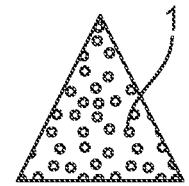
FIG. 2A   FIG. 2B   FIG. 2C
FIG. 3A
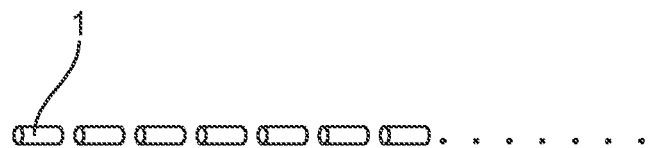
FIG. 3B

DEVICES AND METHODS FOR TREATMENT OF VASCULAR ANEURYSMS

CROSS-REFERENCE TO RELATED APPLICATION

This application is a continuation of U.S. patent application Ser. No. 14/087,980, filed 22 Nov. 2013, which is a continuation and claims the benefit of U.S. patent application Ser. No. 13/663,272, filed 29 Oct. 2012, now issued U.S. Pat. No. 8,647,377, which is a continuation of U.S. patent application Ser. No. 13/533,658, filed 26 Jun. 2012, now issued U.S. Pat. No. 8,535,367, which is a continuation of U.S. patent application Ser. No. 11/552,913, filed 25 Oct. 2006, now issued U.S. Pat. No. 8,231,665, which is a continuation of U.S. patent application Ser. No. 10/301,061, filed 20 Nov. 2002, now abandoned, which claims the benefit of U.S. Provisional Application No. 60/333,373, filed 26 Nov. 2001, which are all incorporated herein by reference in their entireties.

BACKGROUND OF THE INVENTION

The present invention relates to devices and methods for the treatment of diseases in the vasculature, and more specifically, devices and methods for treatment of aneurysms found in blood vessels. Aneurysms can occur in various areas of the cardiovascular system, but are commonly found in the abdominal aorta, thoracic aorta, and cerebral vessels. Aneurysms are unusual ballooning of the vessel due to loss of strength and/or elasticity of the vessel wall. With the constant pulsating pressure exerted on the vessel wall, the diseased or weakened wall can expand out and potentially rupture, which frequently leads to fatality. Prior methods of treating aneurysms have consisted of invasive surgical techniques. The technique involves a major cut down to access the vessel, and the diseased portion of the vessel is replaced by a synthetic tubular graft, Accordingly, this invasive surgical procedure has high mortality and morbidity rates.

Due to the inherent risks and complexities of the surgical procedures, various attempts have been made to develop minimally invasive methods to treat these aneurysms. For treatment of abdominal and thoracic aortic aneurysms, most of the attempts are catheter-based delivery of an endoluminal synthetic graft with some metallic structural member integrated into the graft, commonly called stent-grafts. One of the primary deficiencies of these systems is durability of these implants. Because catheter-based delivery creates limitations on size and structure of the implant that you can deliver to the target site, very thin synthetic grafts are attached to metallic structures, where constant interaction between the two with every heartbeat can cause wear on the graft. Also, the metallic structures often see significant cyclical loads from the pulsating blood, which can lead to fatigue failure of the metallic structure. The combination of a thin fragile graft with a metallic structure without infinite life capabilities can lead to implant failure and can ultimately lead to a fatality.

While the above methods have shown some promise with regard to treating aortic aneurysms with minimally invasive techniques, there remains a need for a treatment system which doesn't rely on the less than optimal combination of a thin graft and metallic structural member to provide long-term positive results. The present invention describes various embodiments and methods to address the shortcomings of current minimally invasive devices and to meet clinical needs.

SUMMARY OF THE INVENTION

In a first aspect, the present invention provides a two part prostheses where one part is an expandable sponge structure and the other part is an expandable tubular mesh structure. The expandable sponge structure is intended to fill the aneurysm cavity to prevent further dilatation of the vessel wall by creating a buffer or barrier between the pressurized pulsating blood flow and the thinning vessel wall. The expandable tubular mesh structure, which is placed across the aneurysm contacting the inner wall of healthy vessel proximal and distal to the aneurysm, serves two purposes. One, it defines the newly formed vessel lumen, even though it does not by itself provide a fluid barrier between the blood flow and the aneurysm. Two, it keeps the expandable sponge structure from protruding out of the aneurysm and into the newly formed vessel lumen. The expandable tubular mesh structure is delivered first across the aneurysm. Then, the expandable sponge structure is delivered via a catheter-based delivery system through a "cell" of the tubular mesh structure and into the aneurysm sac. When the sponge structure is deployed into the aneurysm sac and comes in contact with fluid, it will expand to a size larger than the largest opening or cell of the tubular mesh structure as to prevent the sponge structure from getting out of the aneurysm sac. The filled aneurysm sac will most likely clot off and prevent further dilation of the aneurysm and subsequent rupture. The blood flow should maintain a natural lumen Where the luminal diameter is approximately defined by the diameter of the tubular mesh structure. The advantage of this system is that the sponge filler material acts like a graft but has unparalleled durability. The metallic structure can be optimized for durability as well because the size constraint is somewhat relieved due to the absence of an integrated graft material, which takes up a significant amount of space in a catheter.

In addition, the expandable sponge structure can be used to repair existing endoluminal stent-grafts which have developed leaks. There are thousands of endoluminal stent-grafts implanted into humans to treat abdominal aortic aneurysms. That number is growing daily. The endoluminal stent-grafts are intended to exclude the aneurysm from blood flow and blood pressure by placing a minimally porous graft supported fully or partially by metallic structural members, typically called stents. The acute success rate of these devices is very high, but there are a significant number of these which develop leaks, or blood flow/pressure re-entering the aneurysm sac, some time after the procedure. If the source of the leak can be accessed by the delivery system, the expandable sponge structure can be deployed through that access point.

In another aspect, the present invention provides an inflatable tubular balloon graft. It is a tubular graft, straight or bifurcated, where its wall is not a solid structure but a hollow chamber. The chamber can be filled with a variety of materials which can dictate the mechanical properties of the prostheses. The unfilled tubular balloon graft can be folded and loaded into a catheter-based delivery system, and once in position the tubular balloon graft can be "inflated" with the filler material. The material would be filled in a fluid form and may stay a fluid form or can be solidified by various means such as UV light, heat, and time. The advantage of this system is that a metallic structure is not needed to provide structure to the graft. It is instead replaced by the injectable fluid within the chamber of the tubular balloon graft. Customization of the mechanical properties of the graft is easily accomplished by using balloon fillers of varying properties.

The tubular balloon graft can be completely non-porous, completely porous with same degree of porosity throughout the graft, completely porous with varying porosity within the graft, or partially non-porous and partially porous. Significant porosity on the very outer layer would allow for delivery of an aneurysm sac filling substance or a drug. Porosity on the ends of the graft will help promote cellular in-growth. Porosity on the ends can also he used to deliver an adhesive so that the graft can be securely attached to the vessel wall.

Another embodiment of the tubular balloon graft includes a tubular balloon graft with a bulging outer layer. This will allow the outer surface of the tubular balloon graft to fill some or all of the aneurysm. This will provide a primary or secondary barrier for the aneurysm wall from the pulsating blood flow and will provide a means to prevent migration of the graft due to the enlarged area within the graft. An alternate method of construction would be to attach a bulging outer skin to a standard tubular thin-walled graft and provide a port for injection of the filler substance. Alternatively, instead of a bulging outer skin, a very compliant outer skin can he used so that the volume of material is minimized. The compliant outer skin would be able to expand at very low inflation pressures that would be non-destructive to the aneurysm wall.

BRIEF DESCRIPTION OF THE DRAWINGS

FIGS. 2A-2C illustrate the various cross-sections of the expandable sponge structure.

FIG. 3A illustrates a long continuous sponge structure.

FIG. 3B illustrates multiple short sponge structures.

DETAILED DESCRIPTION OF THE INVENTION

Figure 1A:
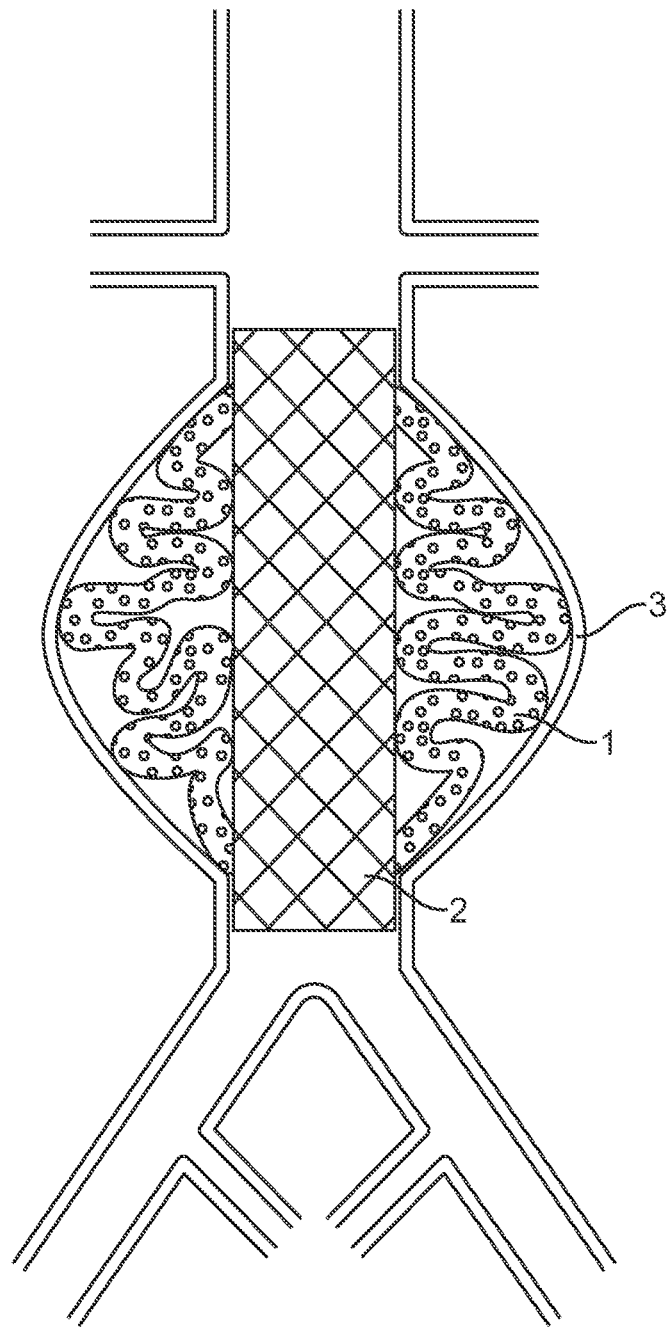
FIG. 1A illustrates the two-part prosthesis.
Figure 1B:
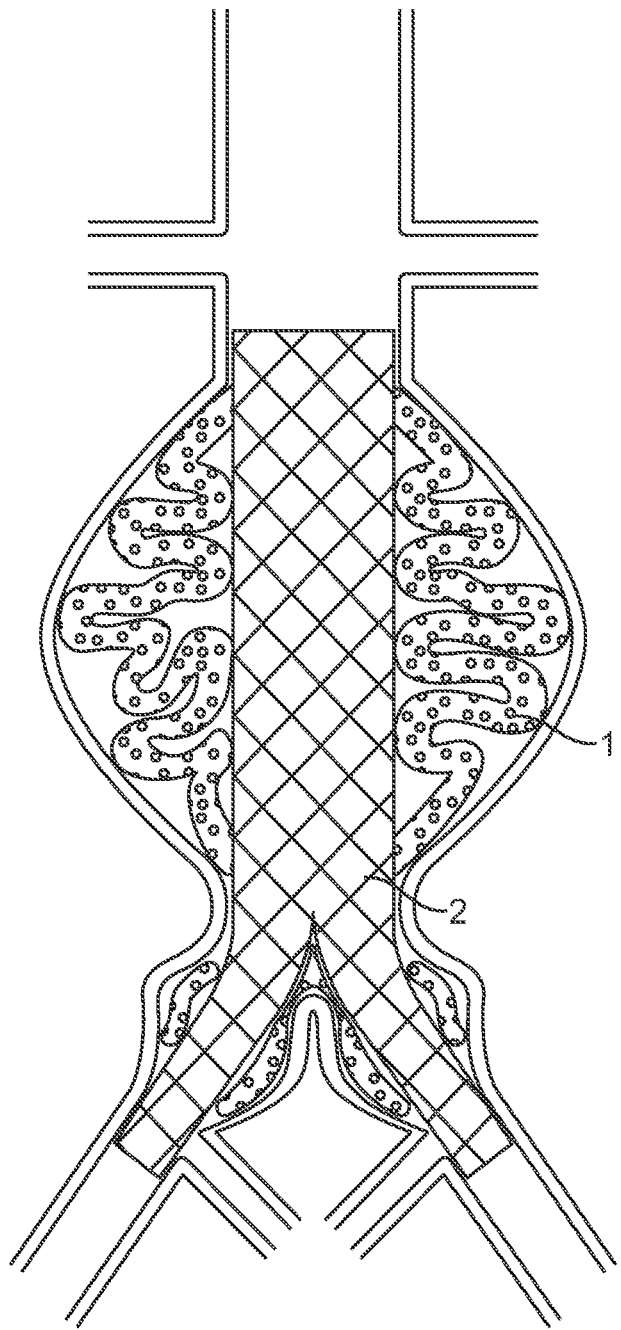
FIG. 1B illustrates a bifurcated version of the expandable tubular mesh structure and the expandable sponge structure.
Figure 1C:
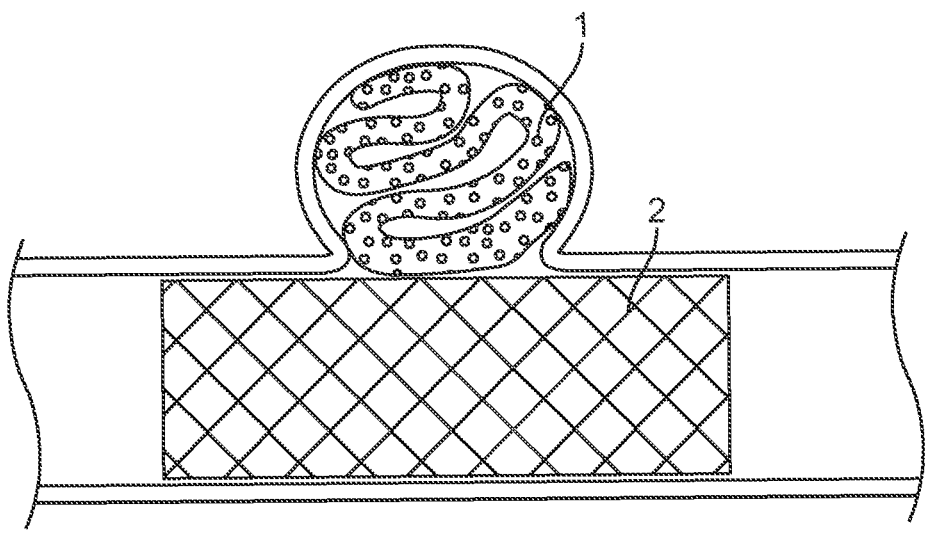
FIG. 1C illustrates an expandable tubular mesh structure placed across an aneurysm and the expandable sponge structure filling up the aneurysm.

FIG. 1A shows the two-part prosthesis comprising of an expandable sponge structure 1 and an expandable tubular mesh structure 2 placed in an abdominal aortic aneurysm 3 located in the infra-renal aorta not involving the iliac arteries. FIG. 1B shows a bifurcated version of the expandable tubular mesh structure 2 and the expandable sponge structure 1 in an abdominal aortic aneurysm located in the infra-renal aorta and involving both iliac arteries. FIG. 1C shows an expandable tubular mesh structure 2 placed across an aneurysm commonly found in cerebral arteries and the expandable sponge structure 1 filling up the aneurysm. The expandable sponge structure 1 is placed through the expandable tubular mesh structure 2 into the aneurysm, filling up the aneurysmal sac which provides a barrier between the thin fragile wall of the aneurysm and the pressurized pulsating blood. The tubular mesh structure 2 keeps the expanded sponge 1 within the confines of the aneurysm and away from the flow path.

The expandable sponge structure 1 is preferably made of common medical grade polymers or natural substances like collagen which can be manufactured into a sponge structure. The sponge structure can be processed in such a way so that it can be compressed to a dry condition size substantially smaller than the wet condition size, exhibiting huge expansion ratio. The expanded sponge structure can take various forms. FIGS. 2A-2C show the various expanded cross-sections that the expandable sponge structure 1 can be. FIG. 2A shows a circular cross section, FIG. 2B shows a square cross section, and FIG. 2C show a triangular cross section. Any cross section can be used. The most important requirement is that it cannot escape from the aneurysm sac through a cell of the expandable tubular mesh structure 2. The length of the expandable sponge structure 1 can vary as well. FIG. 3A shows a long continuous structure 1. And FIG. 3B shows multiple short structures 1.

Figure 4:
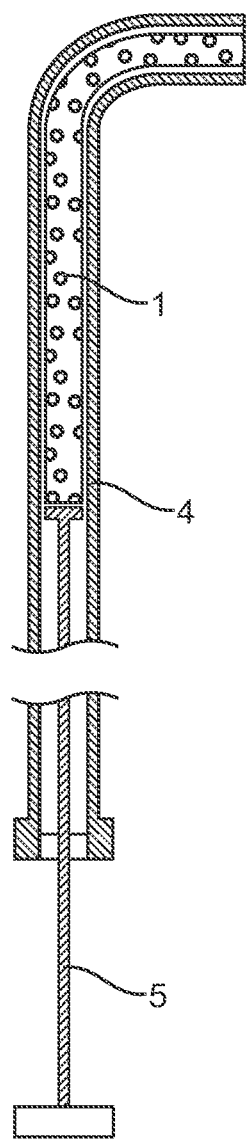
FIG. 4 illustrates the catheter-based delivery system.
Figure 5:
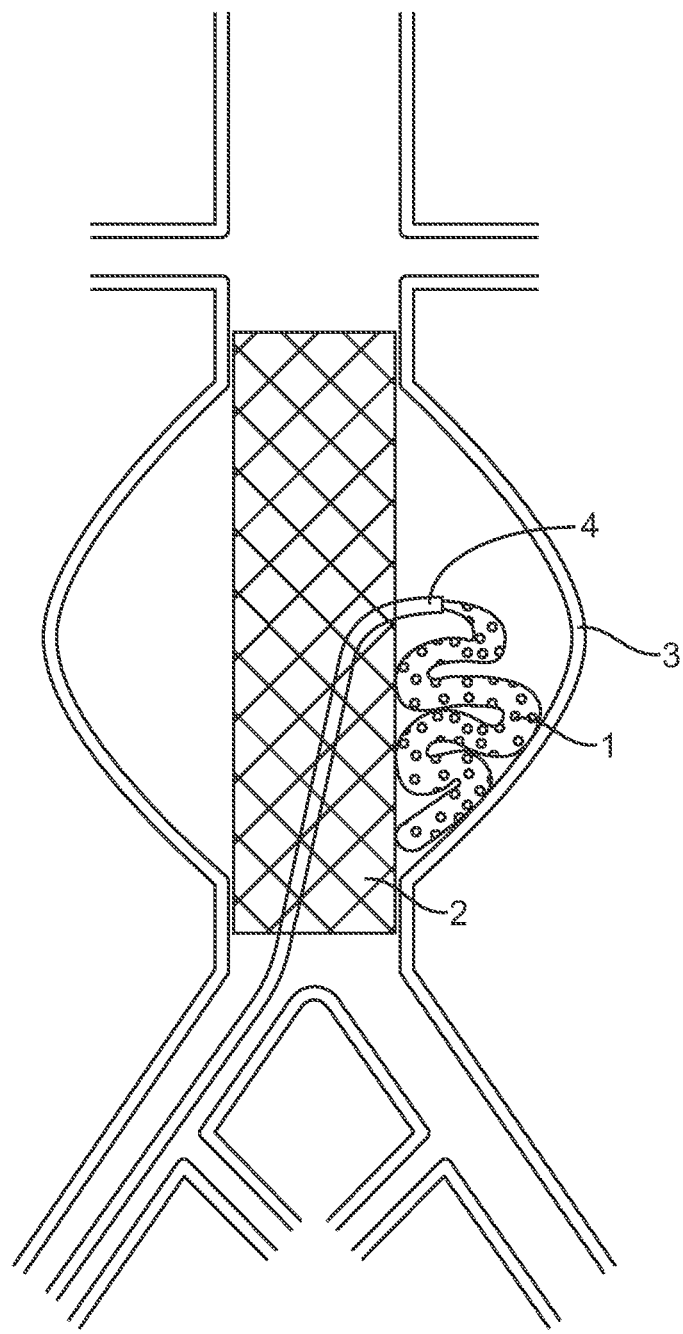
FIG. 5 illustrates a curved delivery catheter.
Figure 6:
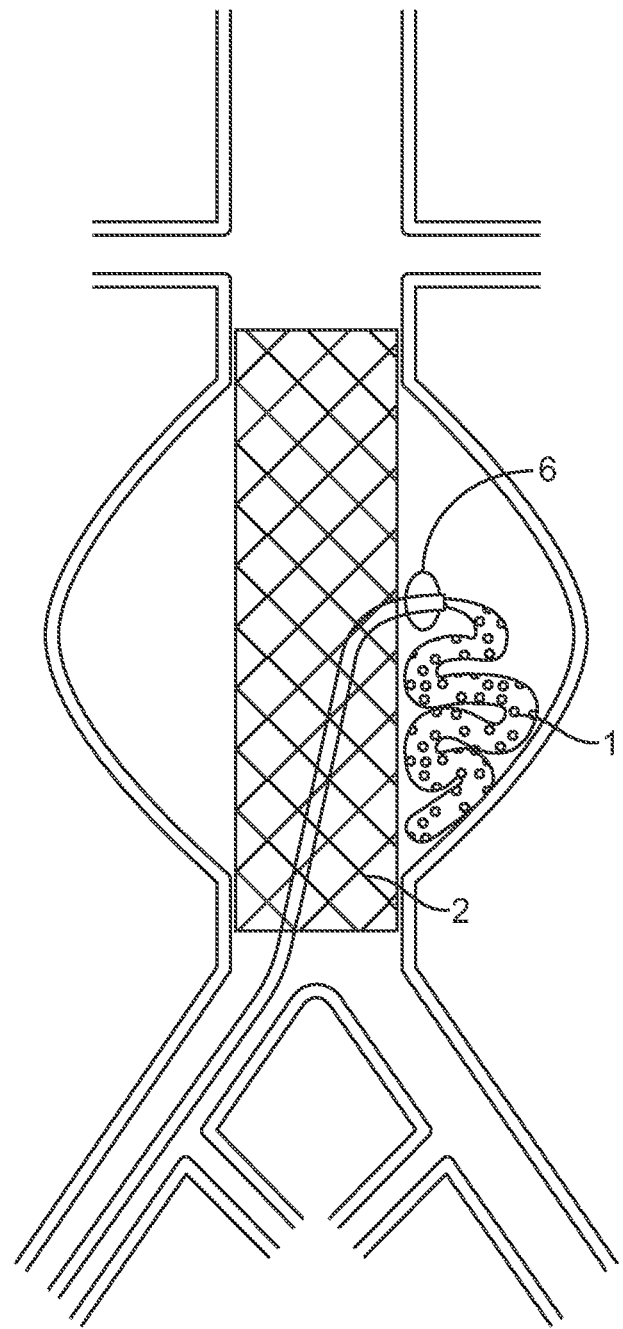
FIG. 6 illustrates a method of ensuring that the delivery catheter's tip stays inside the aneurysm sac.
Figure 7A:
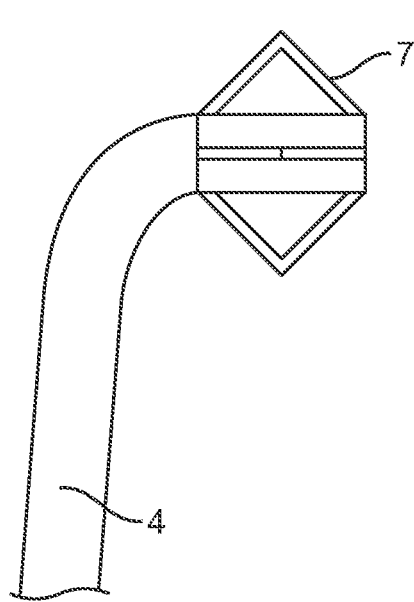
FIG. 7A illustrates an expandable basket-like structure.
Figure 7B:
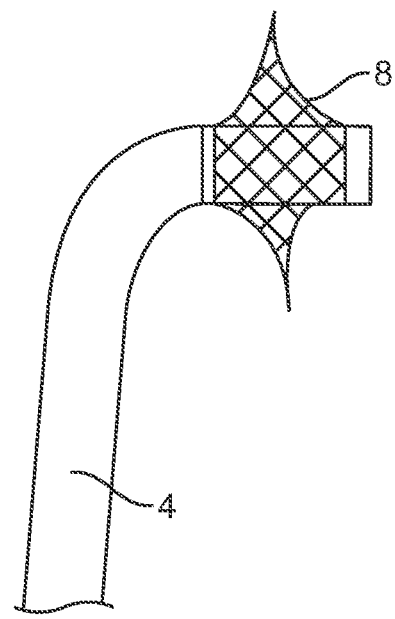
FIG. 7B illustrates an expandable braid-like structure.

One method of delivering the sponge filler 1 into the aneurysm sac is shown by the catheter-based delivery system in FIG. 4. The catheter 4 can hold the compressed sponge 1 within its lumen, and when pushed out with the plunger 5 into the blood filled aneurysm sac, the sponge will expand out to a substantially larger size. The expanded size of the sponge filler is preferably larger than the largest opening of the tubular mesh is structure as to prevent the sponge from escaping the aneurysm sac. FIG. 5 shows an example of a curved delivery catheter 4, where the tip is placed through a cell of the tubular mesh structure 2 and the expandable sponge structure 1 is being deployed into the aneurysm sac. It is important that the tip of the delivery catheter is through a cell of the tubular mesh structure into the aneurysm because the expandable sponge will expand very quickly after being exposed to the blood and being unconstrained by a catheter. FIG. 6 shows a method of ensuring that the delivery catheter's 4 tip stays inside the aneurysm sac by having a balloon 6 on the tip of it, and when inflated after the tip is within the aneurysm sac it will prevent the catheter tip from backing out of the aneurysm sac. FIG. 7A shows an expandable basket-like structure 7 and FIG. 7B shows an expandable braid-like structure 8 which are alternatives to having a balloon 6 on the tip of the catheter 4.

The expandable tubular mesh structure 2 can be made of a metal or of a polymer. The versions made of a metal can be self-expanding from a smaller compressed state or balloon expandable from a smaller compressed or as-cut state. The self-expanding version may be made of metals which exhibit large amounts of elasticity (i.e. nickel-titanium, spring steel, MP-35N and elgiloy) such that when they are compressed down from their expanded state to the compressed state to load into a delivery catheter, they will substantially return to their expanded condition when released from the catheter. Alternatively, shape memory metals like nickel-titanium can be used to provide large expansion ratios. The balloon expandable version may be made of metals which exhibit large permanent deformations without significantly compromising the mechanical performance. The following are some common medical grade metals which are well suited for this purpose: stainless steel, titanium, tantulum, and martensitic nickel titanium. In either the self-expanding or the balloon expandable case, the intent is to deliver the expandable tubular mesh 2 to the target site in a smaller or compressed condition via a catheter-based delivery system so that the target site can be accessed through a remote vascular access point which is conducive to a percutaneous or minimally invasive approach.

Figure 8:
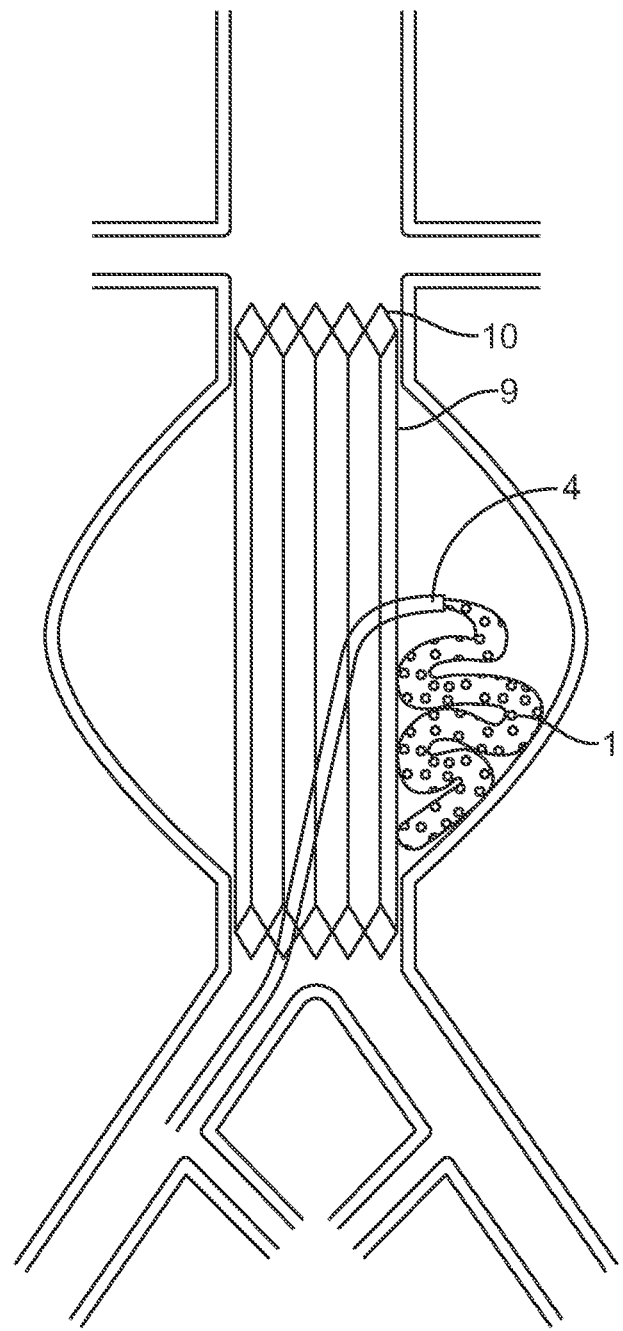
FIG. 8 and 9 illustrate expandable tubular mesh structures.
Figure 9:
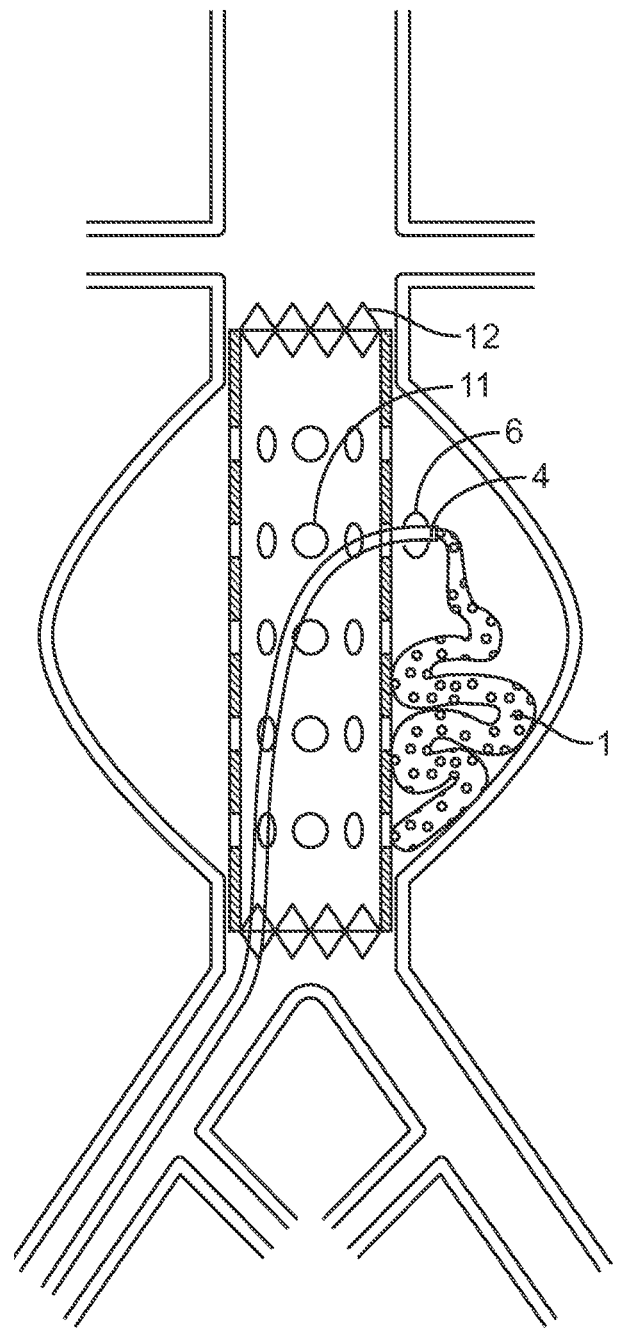

The expandable tubular mesh structure 2 shown in FIGS. 1A, 1B, 1C, 5, and 6 represent a generic mesh structure. FIG. 8 shows an expandable tubular mesh structure where long continuous struts 9 are connected to anchoring end members 10. This allows the structure to be very low in profile in the compressed state, and the durability of this type of structure can be optimized because no radial element exists in the longitudinal struts 9. FIG. 9 show an alternate expandable tubular mesh structure preferably made from a polymer such as PTFE, Polyester, Polyurethane, and the like. The structure has relatively large holes 11 to give access to the expandable sponge delivery catheter. The ends incorporate an anchoring member 12, either self-expanding or balloon expandable.

Figure 10:
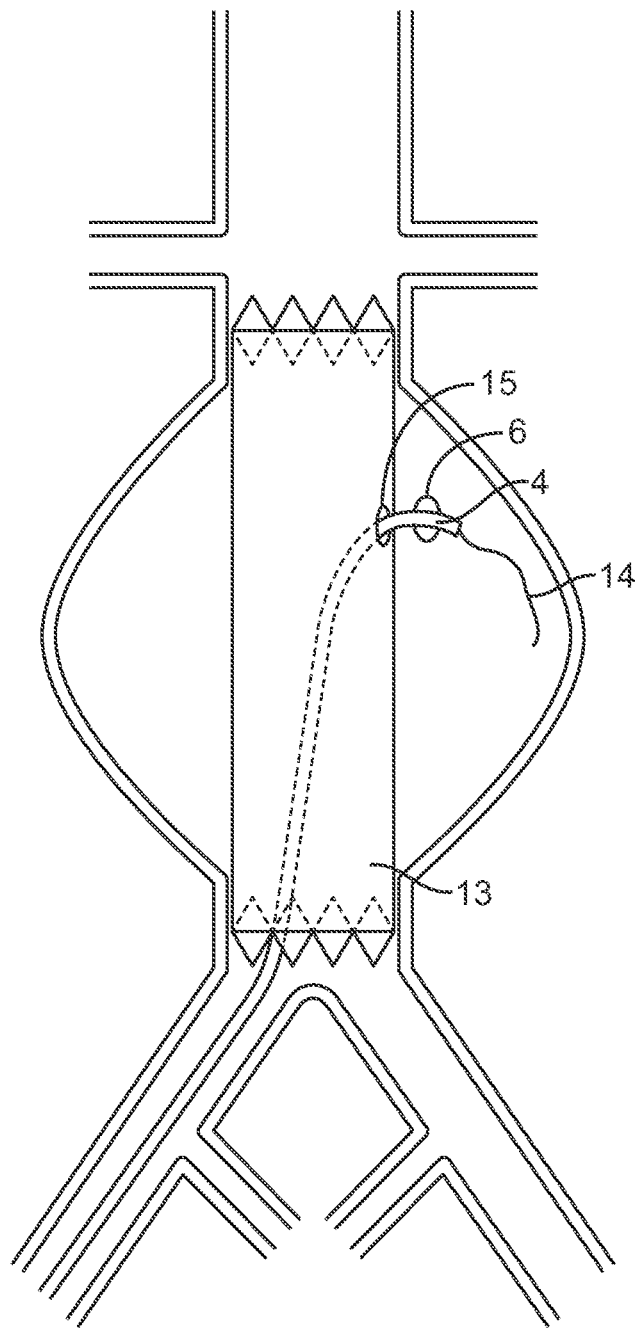
FIG. 10 illustrates a delivery catheter tracked over a guidewire and placed in a stent-graft which developed a leak.
Figure 11:
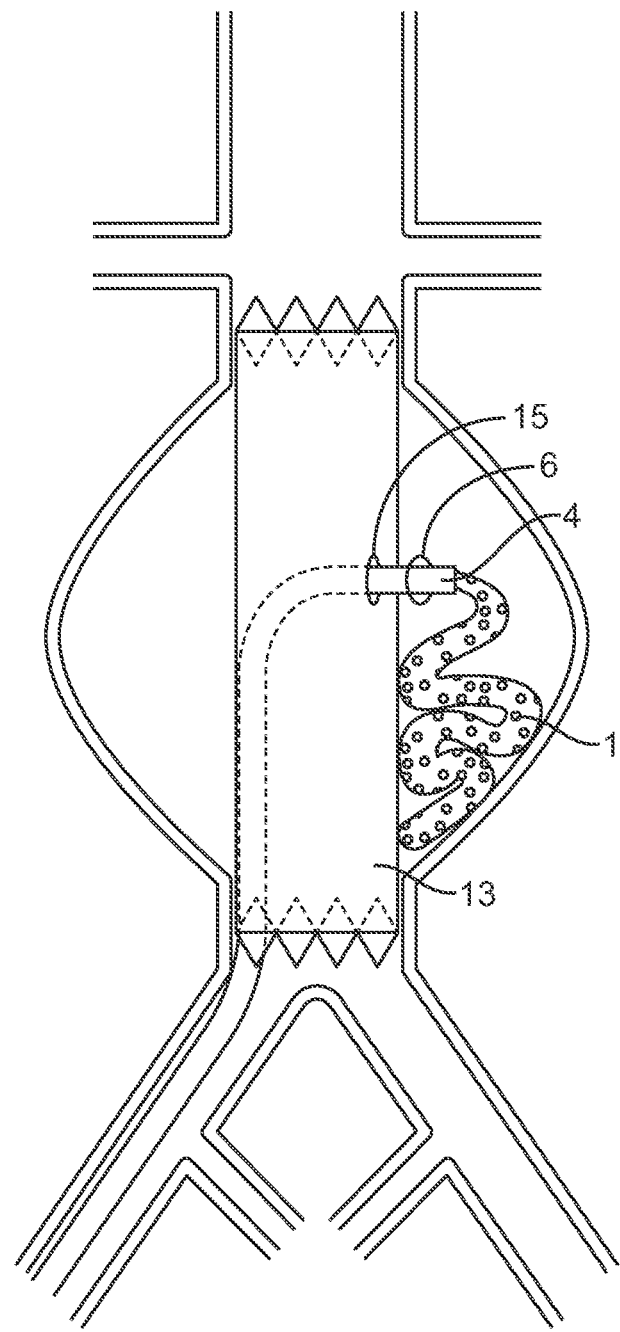
FIG. 11 illustrates the sponge delivered through the delivery catheter.

FIG. 10 shows a delivery catheter 4 which has been tracked over a guidewire 14, which has been placed into the aneurysm sac through an opening 15 of an existing endoluminal stent-graft 13 which developed a leak. The balloon 6 on the delivery catheter 4 was inflated after the delivery catheter 4 was positioned within the aneurysm sac. FIG. 11 shows the guidewire 14 removed, and the expandable sponge structure 1 being delivered through the delivery catheter 4.

Figure 12:
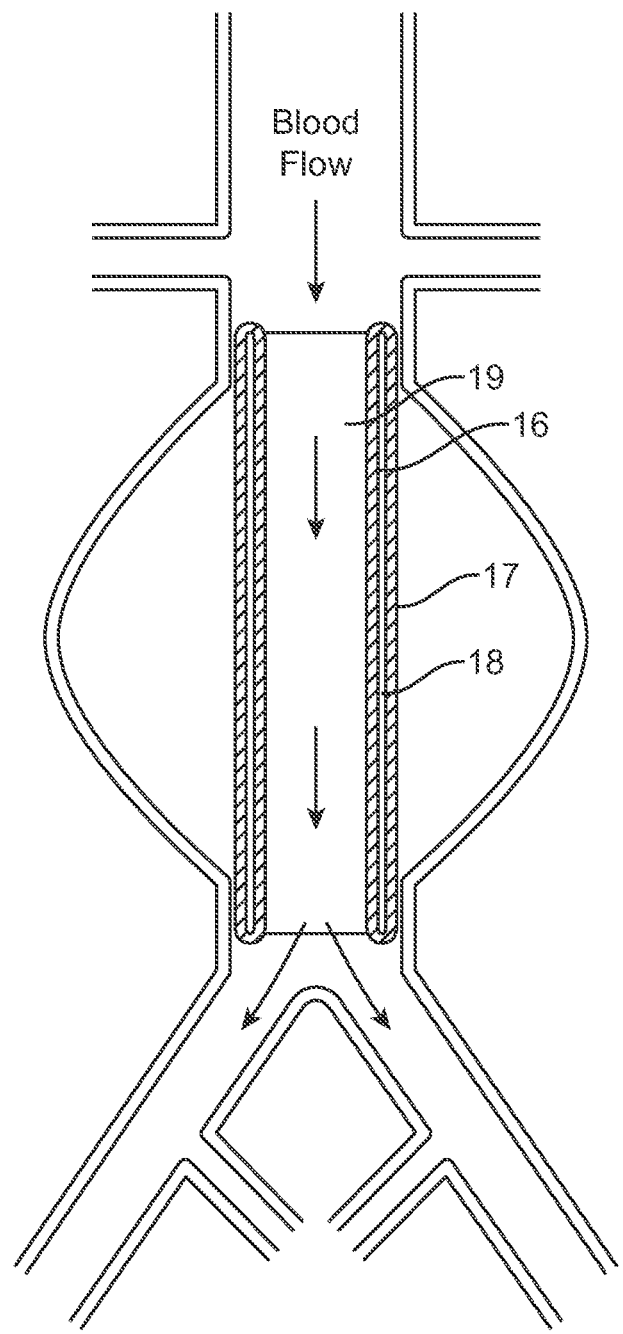
FIGS. 12-15 illustrate tubular balloon grafts.
Figure 13:
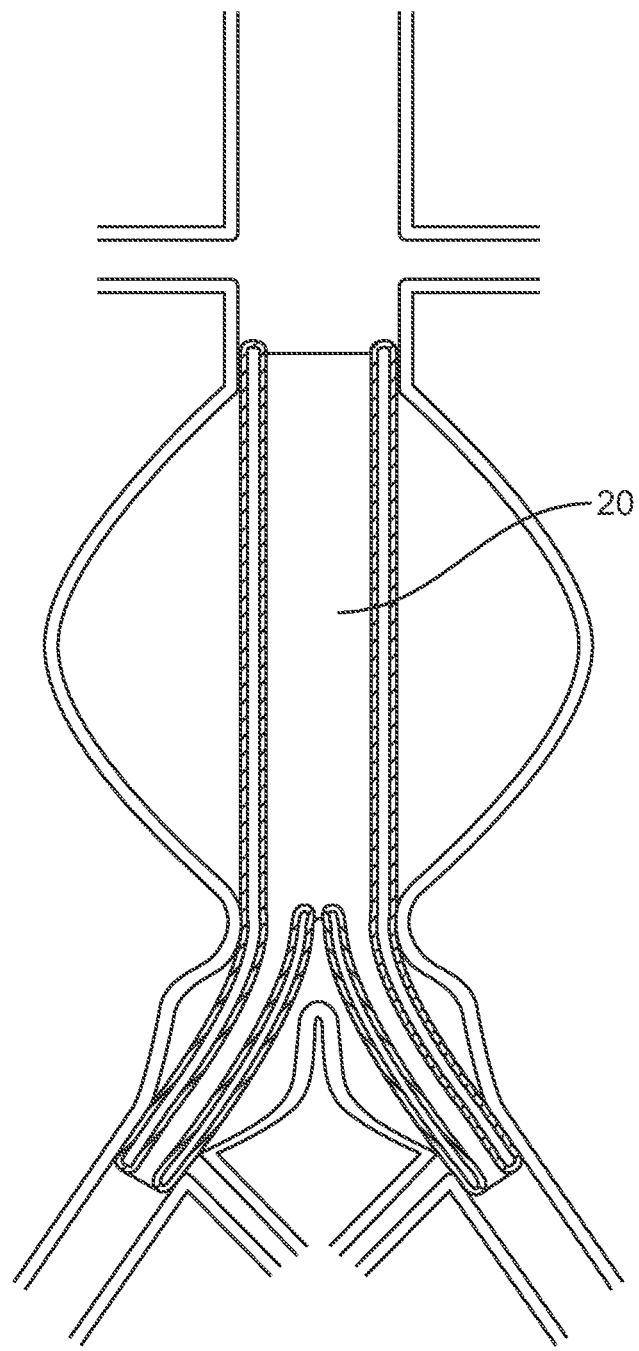

FIG. 12 shows a section view of a tubular balloon graft 19 positioned across an infra-renal aortic aneurysm blocking off the flow to the aneurysm sac. The tubular balloon graft's 19 wall is made of an inner wall 16, an outer wall 17 and a chamber 18 between them. The chamber 18 can be filled with various materials to dictate the mechanical properties of the prosthesis. FIG. 13 shows a bifurcated tubular balloon graft 20 positioned across an infra-renal aortic aneurysm with bi-lateral iliac involvement.

The tubular balloon implant can be made of the various biocompatible materials used to make balloon catheters. Those materials include P.E.T. (Polyester), nylon, urethane, and silicone. It can also be made of other implant grade materials such as ePTFE. One method of making such a device is to start with two thin walled tubes of differing diameters. The difference between the diameters of the tubes will dictate the volume of the balloon chamber. The ends of the tubes can be sealed together with adhesive or by heat to form the balloon chamber. A communication port will be necessary to be able to fill the port with the injected material.

The injected material can be an epoxy, a UV-curable epoxy, silicone, urethane or other type of biocompatible materials such as albumin, collagen, and gelatin glue which is injected into the balloon, and then cured in situ. Or, the injected material doesn't necessarily have to be cured. The as-delivered state may provide the appropriate mechanical properties for the application. Therefore, substances like sterile saline, biocompatible oils, or biocompatible adhesives can be left in the tubular balloon in the as-delivered state.

Figure 14:
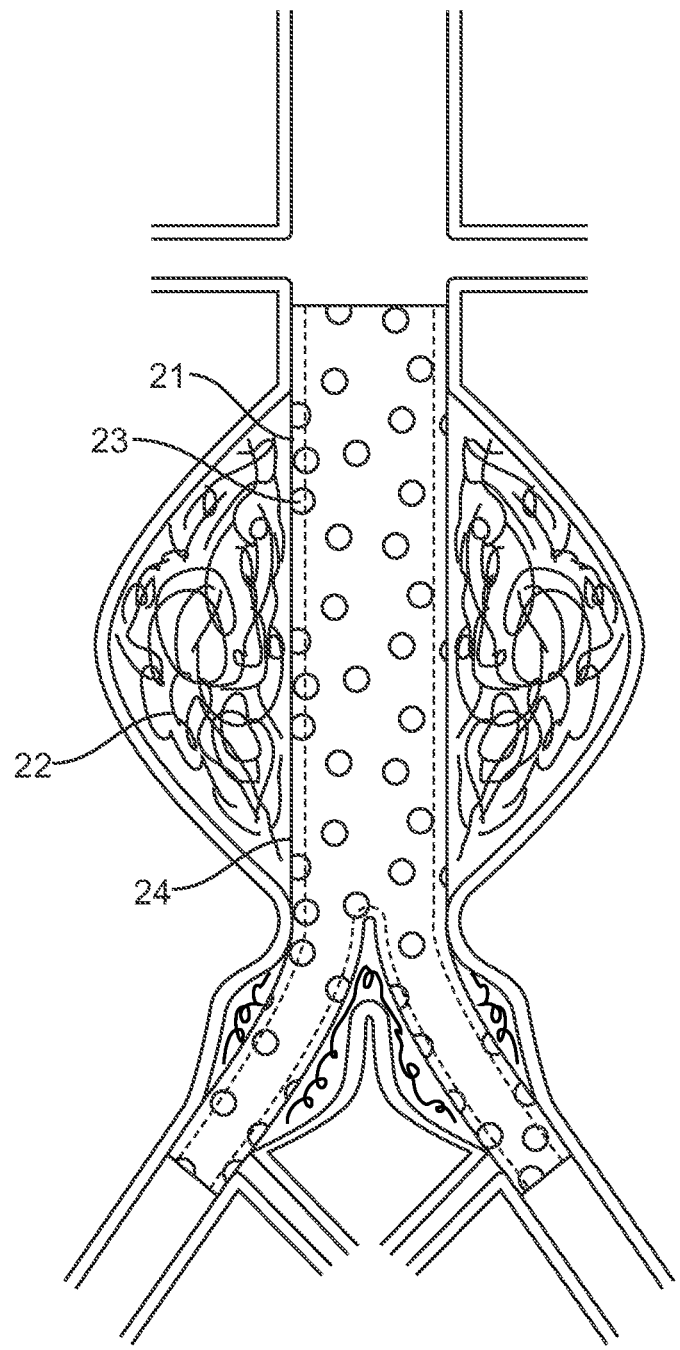
Figure 15:
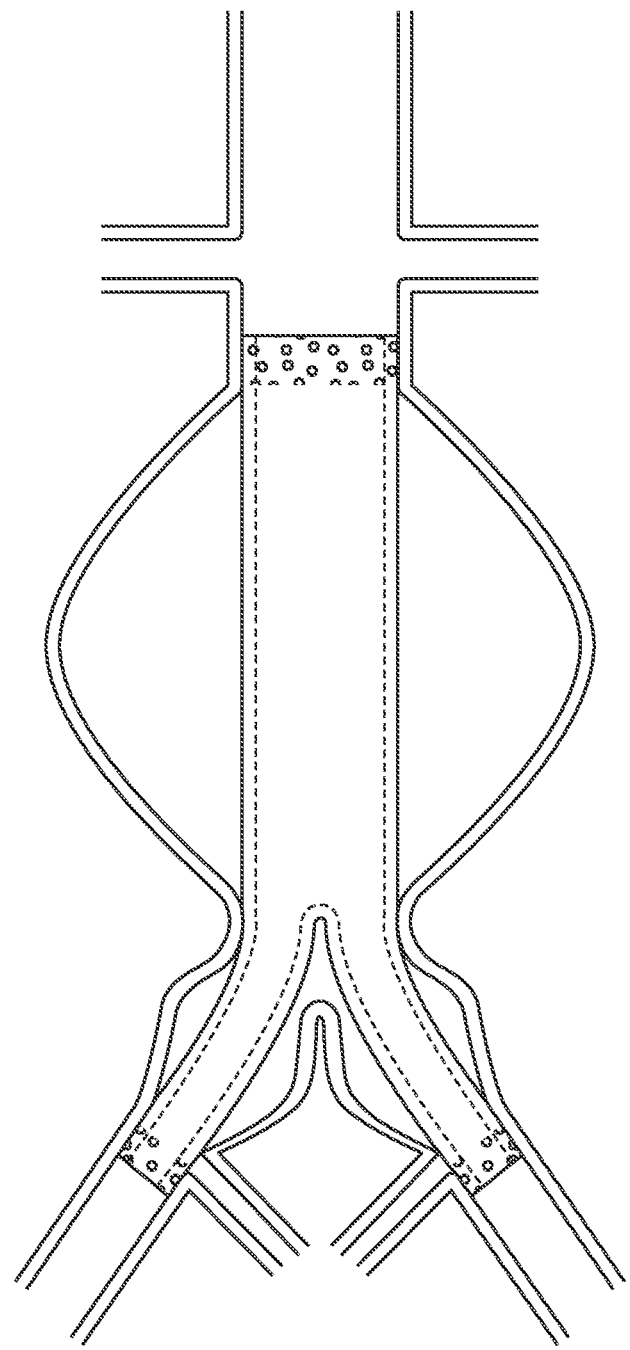

The tubular balloon graft can be non-porous to very porous. FIG. 14 shows a version where the tubular balloon graft has a porous outer wail 24. The chamber 21 of the tubular balloon graft can be used to deliver an aneurysm sac filling substance such as UV curable adhesive 22. The holes 23 which dictate the porosity of the tubular balloon graft can be created with laser drilling, etching, and other methods. The porosity can be varied in select areas of the graft. FIG. 15 shows a tubular balloon graft with only the ends of the graft have porosity to either promote cellular in-growth or to inject an adhesive which allows secure attachment of the graft ends to the vessel wall.

Figure 16:
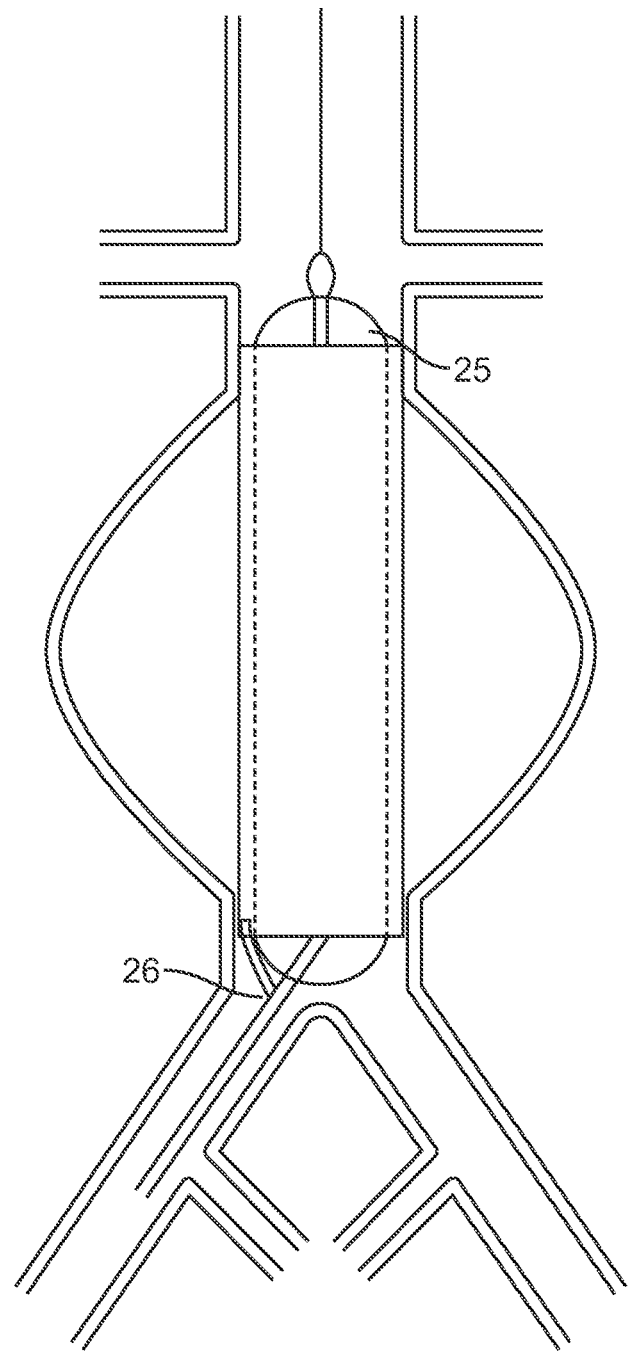
FIGS. 16 and 17 illustrate tubular balloon grafts being expanded.
Figure 17:
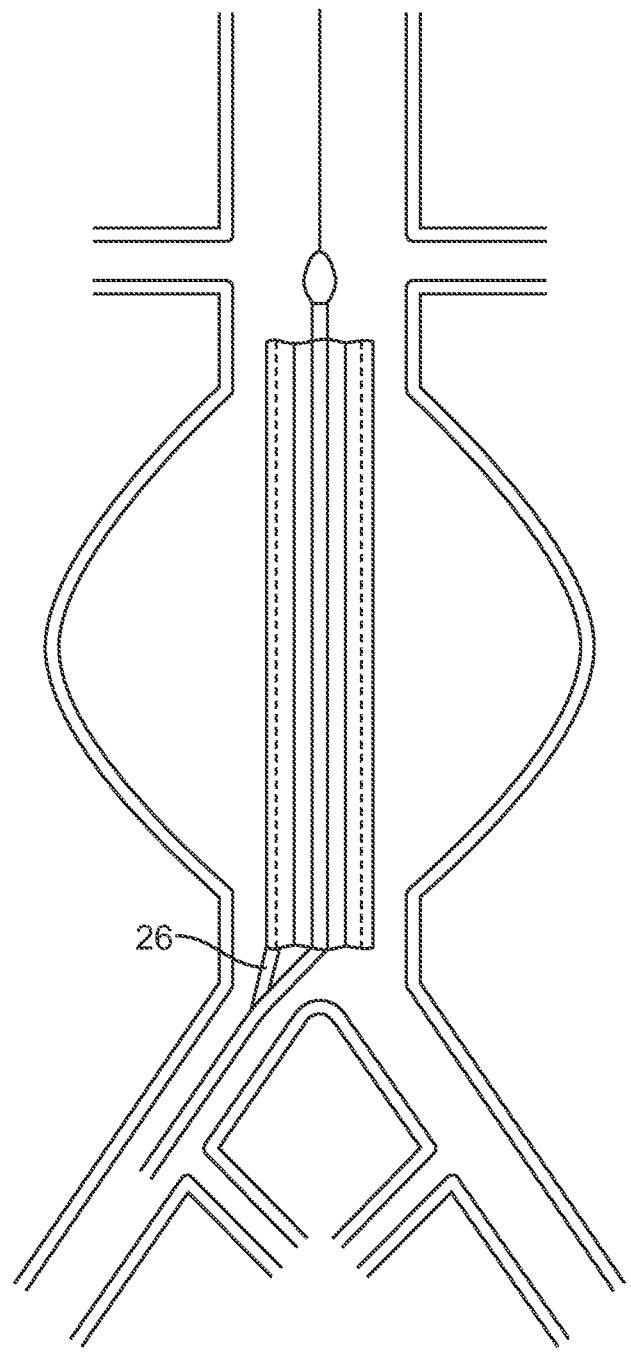

FIG. 16 shows a tubular balloon graft 19 which is being expanded from a folded condition (not shown) by a balloon catheter 25. Once expanded, the chamber 18 of the tubular balloon graft 19 can be filled with the desired substance through the chamber access port 26. FIG. 17 shows a tubular balloon graft 19 being expanded by an inflation process or filling the chamber 18 of the tubular balloon graft 19 through the chamber access port 26.

Figure 18:
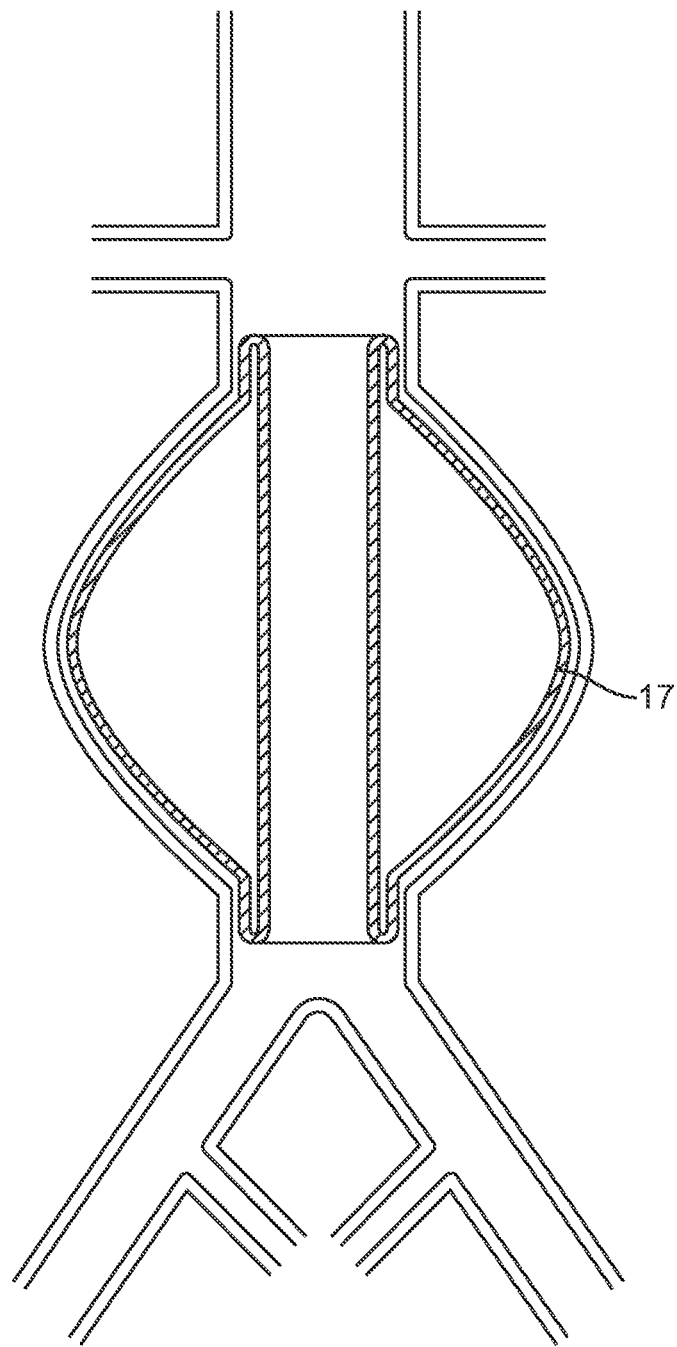
FIG. 18 illustrates a tubular balloon graft.
Figure 19:
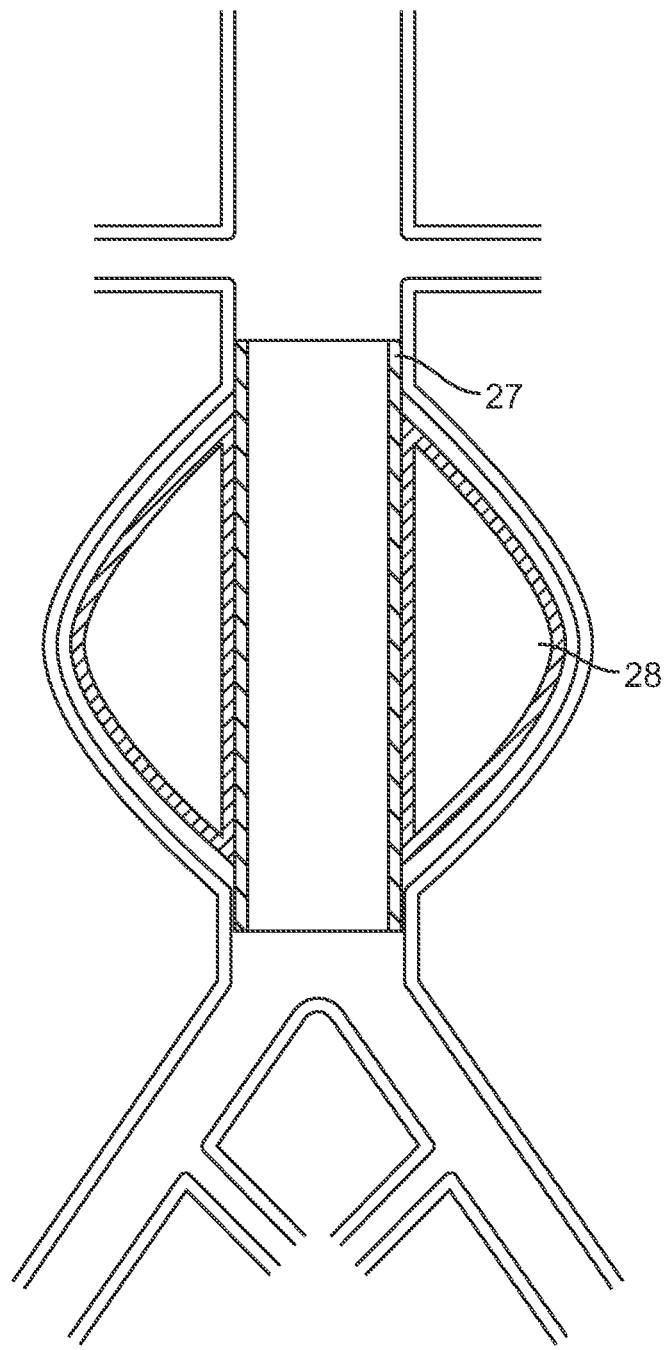
FIGS. 19, 20A and 20B illustrate a vascular graft with an integrated tubular balloon.
Figure 20A:
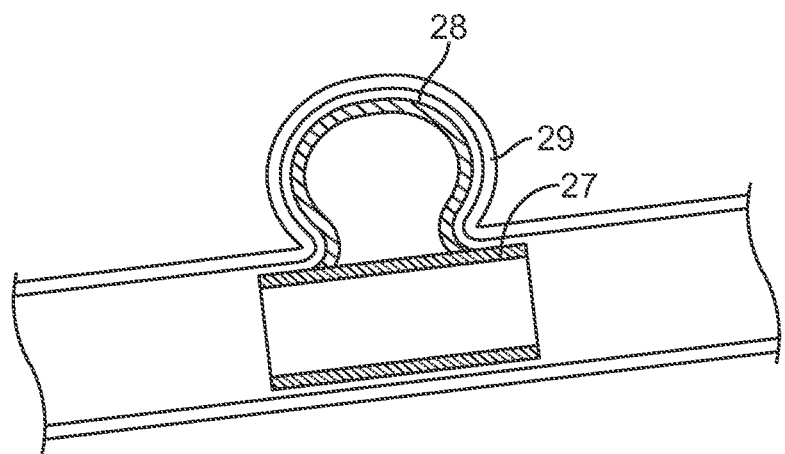
Figure 20B:
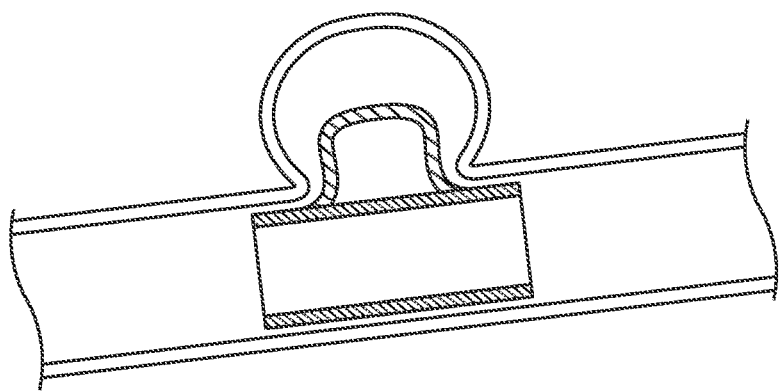

FIG. 18 shows a version of the tubular balloon graft with an outer wall 17 which is substantially bulged out so that it fills some or all of the aneurysm sac. FIG. 19 shows a vascular graft 27 which has an integrated balloon 28 attached to the outside surface of the graft. The balloon can be pre-bulged and folded down for delivery, or it can be a very compliant material like silicone, urethane, or latex so that it has no folds whether compressed or expanded. FIG. 20A shows the same type of implant, a graft 27 with an external balloon 28, used in a cerebral vessel aneurysm 29. FIG. 20B show the same implant as 20A, except that the implant balloon does not fully fill the aneurysm, which can be acceptable because the graft 27 excludes the aneurysm from the blood flow, and the primary purpose of the balloon 28 is to prevent migration of the graft 27.

The graft 27 can be made of commonly used implant polymers such as PTFE, Polyester, Polyurethane, etc. The balloon 28 surrounding the graft can be made of the same commonly used vascular implant materials as well. The graft and balloon materials can be different, but it is commonly known that using the same material for both would facilitate processing/manufacturing. The theory is that the balloon 28 would preferentially only deploy into the aneurysm sac where the resistance to expansion is minimal as compared to the vessel wall. The graft 27 would provide the primary barrier between the pressurized blood and the thin wall of the aneurysm. Secondarily, the balloon itself provides a buffer from the pressurized blood. The balloon's 28 primary function, however, is to hold the graft 27 in place. Since the expanded section of the implant is "locked" into the aneurysm, the graft 27 should not migrate. Also, the balloon 28, in the filled state, will provide hoop strength to the graft 27.

Figure 21A:
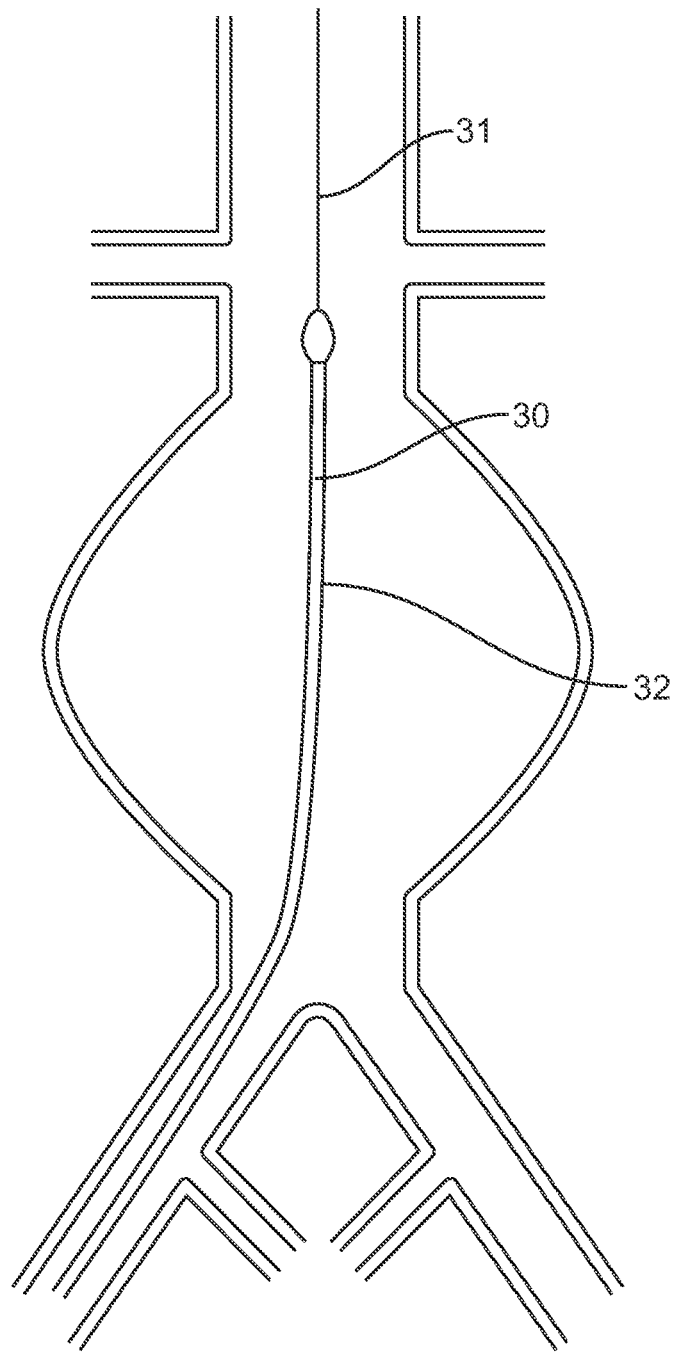
FIGS. 21A-21E illustrate a method of delivering a graft with an external balloon.
Figure 21B:
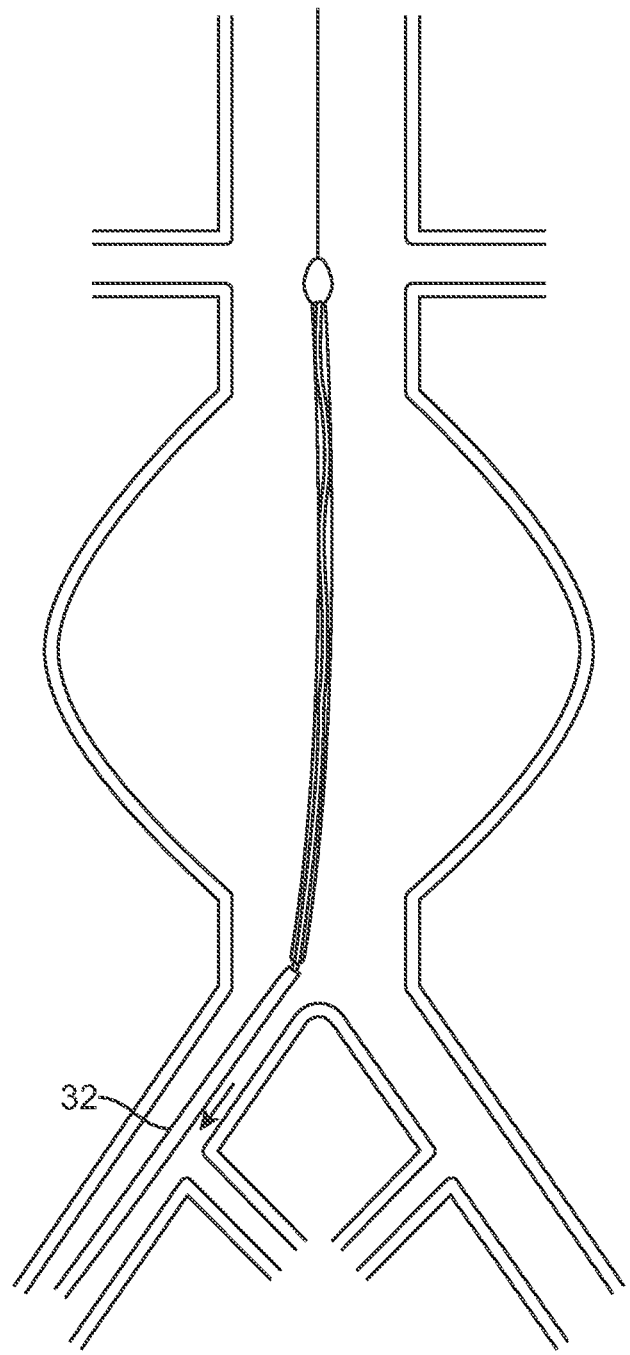
Figure 21C:
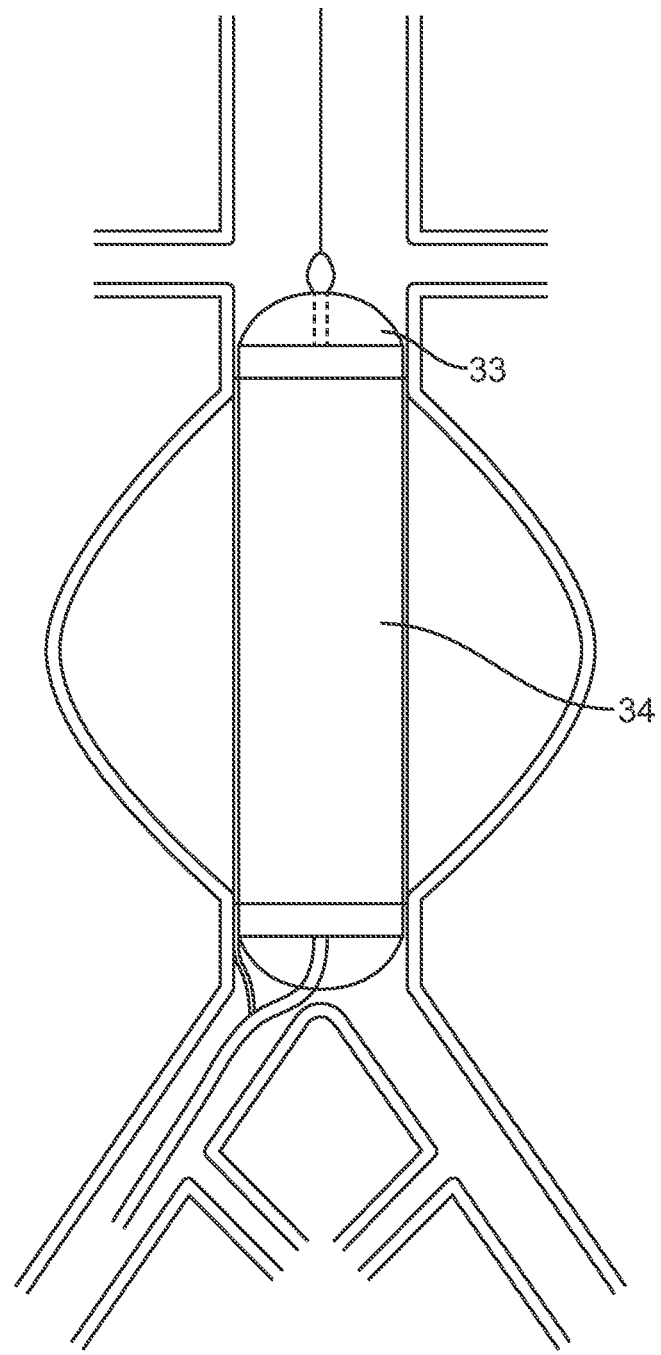
Figure 21D:
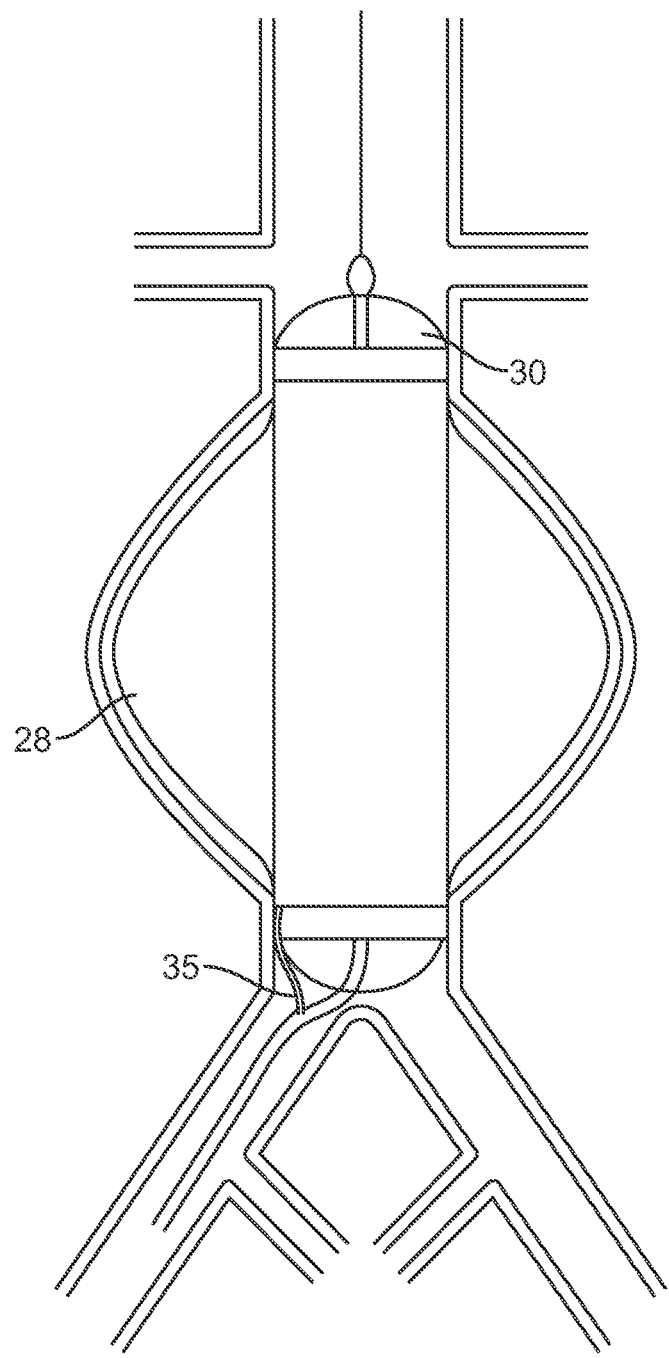
Figure 21E:
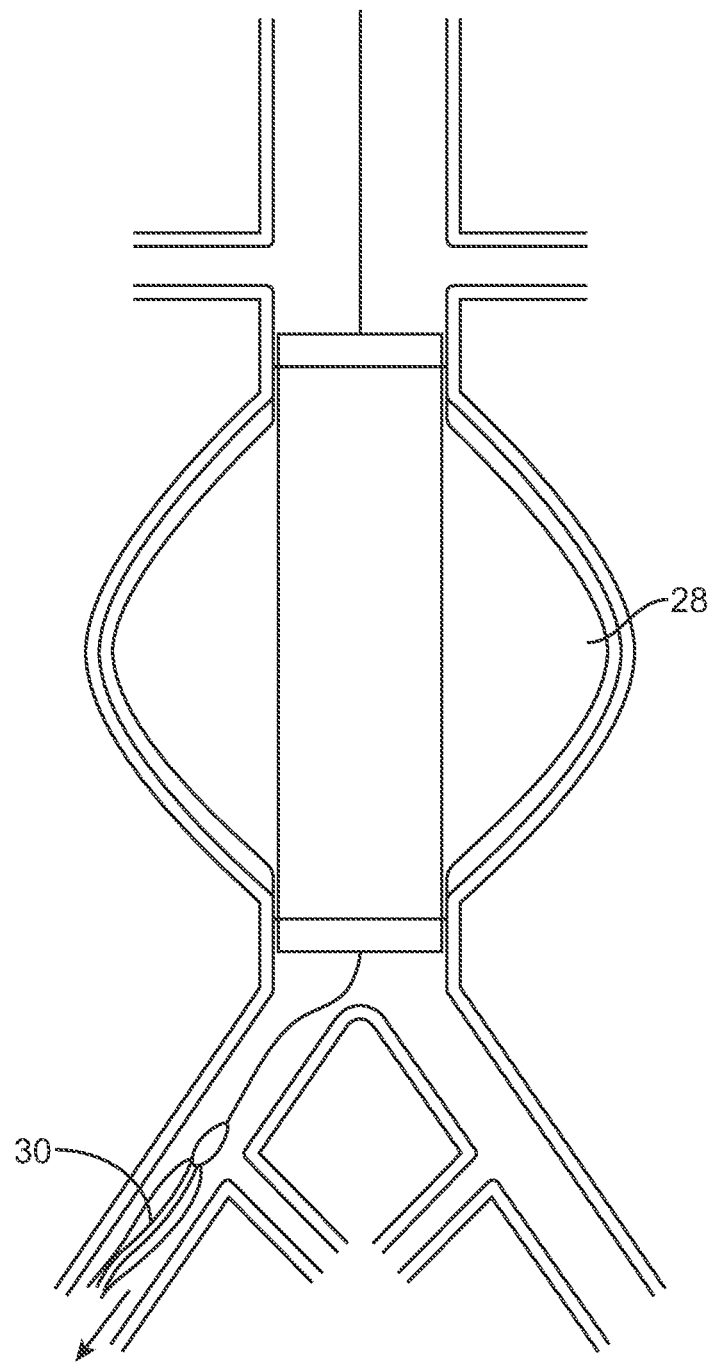

FIGS. 21A-21E demonstrate one method of delivering a graft with an external balloon to the target site. FIG. 21A shows the implant loaded onto a balloon delivery catheter 30 with an outer sheath 32 and positioned over a guide wire 31 at the aneurysm target site. FIG. 21B shows that once in position, the outer sheath 32 is withdrawn. FIG. 21C shows the balloon delivery catheter 33 being inflated, pushing the implant 34 against the healthy vessel walls on both sides of the aneurysm. FIG. 21D shows that the balloon delivery catheter 30 may also have an implant balloon inflation port 35 which can now be used to fill up the implant balloon 28 with a biocompatible substance. The substance can be sterile saline, contrast agent, hydrogel, and UV cure adhesive to name a few. Most likely, low inflation pressures would be used to fill the implant balloon 28. FIG. 21E shows that once the implant balloon 28 is filled, the implant balloon inflation port 35 can be detached and the delivery catheter 30 removed.

We claim:

1. A method for treating an aneurysm comprising:
placing a stent across the aneurysm, the stent comprising a first end, a second end, and an outside surface between the first and second ends;
delivering an elongated piece of expandable foam between the outside surface of the stent and a tissue surface of the aneurysm, the elongated piece increasing in length during delivery from a first length to a second length and comprising bends; and
during the delivering step, exposing the elongated piece of expandable foam to a fluid to expand the elongated piece of expandable foam such that as the elongated piece of expandable foam is delivered and increases in length it becomes exposed to the fluid and expands,
wherein the elongated piece of expandable foam comprises a continuous foam structure when expanded,
wherein the continuous foam structure partially or completely fills the aneurysm,
wherein the continuous foam structure contacts a portion of the aneurysm wall and a portion of the outside surface of the stent; and
wherein the stent prevents the elongated piece of expandable foam from protruding out of the aneurysm into a vessel lumen.

2. The method of claim 1, wherein the stein comprises an expandable tubular mesh.

3. The method of claim 1, wherein the elongated piece of expandable foam comprises a sponge.

4. The method of claim 1, wherein the fluid comprises blood.

5. The method of claim 1, wherein the elongated piece of expandable foam comprises collagen, wherein the collagen has a compressed configuration when the collagen is in a dry condition, and an expanded configuration when the collagen is in a wet condition.

6. The method of claim 1, wherein the elongated piece of expandable foam comprises a polymer, wherein the polymer has a compressed configuration when the polymer is in a dry condition, and an expanded configuration when the polymer is in a wet condition.

7. The method of claim 1, wherein an expanded cross-section of the elongated piece of expandable foam comprises a circular, square, or triangular cross-section.

8. The method of claim 1, wherein the elongated piece of expandable foam when expanded comprises an outer foam surface having pores and an inner foam structure within the outer foam surface.

9. A method for treating an aneurysm comprising:
placing a stent across the aneurysm, the stent comprising a first end, a second end, and an outside surface between the first and second ends;
placing a catheter delivery system between the first end and the second end, wherein a tip of the catheter delivery system is in between the outside surface of the stent and the confines of the aneurysm;
delivering an expandable foam into the catheter delivery system;
deploying, from the catheter delivery system, a continuous length of the expandable foam into the confines of the aneurysm; and
exposing the expandable foam to a fluid to expand the expandable foam,
wherein the continuous length of the expandable foam comprises folds after deployment;
wherein the continuous length of the expandable foam when expanded comprises a single foam structure in contact with a graft wall or a portion of the outside surface of the stent, the aneurysm wall, the proximal end of the aneurysm, and the distal end of the aneurysm, and
wherein the stent prevents the continuous length of the expandable foam from protruding out of the aneurysm into a vessel lumen.

10. The method of claim 9, wherein the stent comprises an expandable tubular mesh.

11. The method of claim 9, wherein the stent comprises cells, and wherein an expanded cross-section of the continuous length of the expandable foam has a size larger than any cell of the stent.

12. The method of claim 9, wherein the expandable foam comprises collagen or a polymer.

13. The method of claim 9, wherein the stent comprises a cell, the method further comprising:
delivering the expandable foam via the catheter delivery system through the cell of the stent, and
passing the tip of the catheter delivery system through the cell of the stent.

14. The method of claim 13, wherein the tip of the catheter delivery system comprises an expandable structure positioned on the tip of the catheter delivery system configured to prevent the tip from backing out of the aneurysm.

15. The method of claim 13, further comprising passing the expandable foam through a communication port coupled to the catheter delivery system.

16. The method of claim 9, wherein the catheter delivery system contains the expandable foam before the expandable foam is deployed into the aneurysm.

17. The method of claim 9, wherein the expandable foam comprises a sponge.

18. The method of claim 9, wherein the continuous length of expandable foam when expanded comprises an outer foam surface having pores and an inner foam structure within the outer foam surface.

19. A method for treating an aneurysm comprising:
placing a stent across the aneurysm, the stent comprising a first end, a second end, and an outside surface between the first and second ends;
delivering a length of expandable foam having a bend between the outside surface of the stent and the confines of the aneurysm away from a blood flow path;
creating, during the delivering step, the bend in the length of expandable foam; and
exposing the length of expandable foam to a fluid to expand the expandable foam,
wherein the length of expandable foam comprises a polymer,
wherein the stent prevents the length of expandable foam from protruding out of the aneurysm into a vessel lumen.

20. The method of claim 19, wherein the length of expandable foam comprises a continuous foam structure when expanded, wherein the continuous foam structure partially or completely fills the aneurysm, and wherein only one length of expandable foam is delivered to partially or completely fill the aneurysm.

* * * * *